(12) United States Patent
Koyama et al.

(10) Patent No.: US 8,518,669 B2
(45) Date of Patent: Aug. 27, 2013

(54) RECOMBINANT EXPRESSION PLASMID VECTOR AND RECOMBINANT STRAIN TO BE USED IN PRODUCING OXALATE DECARBOXYLASE, AND METHOD OF PRODUCING RECOMBINANT OXALATE DECARBOXYLASE

(75) Inventors: Takahumi Koyama, Kakamigahara (JP); Yuzo Kojima, Kakamigahara (JP); Kenji Kojima, Kakamigahara (JP); Masashi Minoda, Konan (JP)

(73) Assignee: Amano Enzyme Inc., Nagoya-Shi (JP)

( * ) Notice: Subject to any disclaimer, the term of this patent is extended or adjusted under 35 U.S.C. 154(b) by 249 days.

(21) Appl. No.: 12/811,573

(22) PCT Filed: Nov. 26, 2008

(86) PCT No.: PCT/JP2008/071403
§ 371 (c)(1),
(2), (4) Date: Oct. 7, 2010

(87) PCT Pub. No.: WO2009/087826
PCT Pub. Date: Jul. 16, 2009

(65) Prior Publication Data
US 2011/0020938 A1 Jan. 27, 2011

(30) Foreign Application Priority Data
Jan. 4, 2008 (JP) .................. 2008-000075

(51) Int. Cl.
*C12P 21/02* (2006.01)
*C12N 15/00* (2006.01)
*C12N 9/88* (2006.01)

(52) U.S. Cl.
USPC ............... 435/71.2; 435/320.1; 435/232

(58) Field of Classification Search
None
See application file for complete search history.

(56) References Cited

PUBLICATIONS

MacClellan et al., Mol. Microbiol. 69(4): 954-967, 2008.*
Tanner, A. et al., "Oxalate Decarboxylase Requires Manganese and Dioxygen for Activity," Journal of Biological Chemistry, 2001, vol. 276, No. 47, pp. 43627-43634.
Fahnestock, S. R. et al., "Expression of the Staphylococcal Protein a Gene in *Bacillus subtilis* by Gene Fusions Utilizing the Promoter from a *Bacillus amyloliquefaciens* α-Amylase Gene," Journal of Bacteriology, 1986, vol. 165 No. 3, pp. 796-804.
Ulmanen, I., et al., "Transcription and Translation of Foreign Genes in *Bacillus subtilis* by the Aid of a Secretion Vector," Journal of Bacteriology, 1985, vol. 162 No. 1, pp. 176-182.
Yamane, K. "Yuyo Biseibutsu no. Kairyo Gijutsu no Kaihatsu - Karekusakin no Bunpitsukei o Mochiita Koso no. Ryosanka-", The Ministry of Agriculture, Forestry and Fisheries of Japan Ogata Tokubetsuwaku Kenkyu Biomass Henkan Keikaku Showa 61 Nendo Itaku Jigyo Hokokusho, 1987, pp. 1-19 and cover page.
Xiao, L., et al., "Highly efficient gene expression of a fibrinolytic enzyme (subtilisin DFE) in *Bacillus subtilis* mediated by the promoter of α-amylase gene from *Bacillus amyloliquefaciens*," Biotechnol. Lett., 2004, vol. 26, pp. 1365-1369.
Miles, J.S., et al, "*Bacillus subtilis* 42.7kB DNA fragment from yvsA to yvqA," Database GenBank, Accession No. AJ223978, 2005 Internet <URL:http://www.ncbi.nlm.nih.gov/entrez/viewer.fcgi?db=nuccore&id=2832786>, Definition: *Bacillus subtilis* 42.7kB DNA.fragment, 16 pages.
Tanner, A., et al., "*Bacillus subtilis* YvrK is an Acid-Induced Oxalate Decarboxylase," Journal of Bacteriology, 2000, vol. 182, No. 18, pp. 5271-5273.
International Search Report dated Dec. 22, 2008, issued on PCT/JP2008/071403.
Ilkka Palva et al., "Nucleotide sequence of the promoter and NH$_2$-terminal signal peptide region of the α-amylase gene from *Bacillus amyloliquefaciens*," Gene. 15(1981), pp. 43-51.
"*Bacillus subtilis* 42.7kB DNA fragment from yvsA to yvqA," GenBank GI:2832786, 2005, pp. 1-24.
Office Action dated Aug. 17, 2011, issued for the corresponding Chinese patent application No. 200880123693.6 and English abstract thereof.

* cited by examiner

*Primary Examiner* — Nancy T Vogel
(74) *Attorney, Agent, or Firm* — Edwards Wildman Palmer LLP; James E. Armstrong, IV; Edmund J. Koundakjian

(57) ABSTRACT

An object is to provide a means of highly producing an oxalate decarboxylase originating in a microorganism. A recombinant expression plasmid vector, which contains an α-amylase promoter belonging to the genus *Bacillus* and an oxalate decarboxylase gene originating in a microorganism that is provided under the control of the promoter, is constructed. A host bacterium is transformed with this vector to prepare an oxalate decarboxylase producing bacterium. A recombinant oxalate decarboxylase is produced by culturing the producing bacterium and then recovering the oxalate decarboxylase thus produced.

20 Claims, 15 Drawing Sheets

FIG.1

| Host | Promoter |
|---|---|
| B. subtilis 168 strain | amy Promoter |
| E. coli JM109 strain | lac Promoter |

*FIG.13*

| No. | Host | Promoter | Others | OXDC productivity per culture liquid (mg/L) *Ratio to wild stain No. 7 is shown in parentheses | OXDC productivity per culture liquid (mg/g) *Ratio to recombinant bacterium No. 8 is shown in parentheses |
|---|---|---|---|---|---|
| 1 | B. subtilis 168 | amy | — | 1,560 (3,900 times) | 84.3 (30.1 times) |
| 2 | E. coli JM109 | lac | — | 114 (285 times) | 8.8 (3.1 times) |
| 3 | B. subtilis 168 | mutated amy | — | 2,170 (5,425 times) | 103.3 (36.9 times) |
| 4 | B. subtilis 168 | mutated amy | with yvrL | 1,300 (3,250 times) | 54.2 (19.3 times) |
| 5 | E. coli JM109 | amy | — | 198 (495 times) | 10.3 (3.7 times) |
| 6 | E. coli JM109 | mutated amy | — | 360 (900 times) | 17.5 (6.3 times) |
| 7 | Wild strain | | — | 0.4 (—) | - |
| 8 | Reported recombiant Escherichia coli (J. Biol. Chem. 276 (2001), 43627-43634) | | with yvrL | — | 2.8 (—) |

SEQUENCE LISTING

```
<160> NUMBER OF SEQ ID NOS: 21

<210> SEQ ID NO 1
<211> LENGTH: 1158
<212> TYPE: DNA
<213> ORGANISM: Bacillus subtilis

<400> SEQUENCE: 1
atgaaaaaac aaaatgacat tccgcagcca attagaggag acaaaggagc aacggtaaaa      60
atcccgcgca atattgaaag agaccggcaa aaccctgata tgctcgttcc gcctgaaacc     120
gatcatggca ccgtcagcaa tatgaagttt tcattctctg atactcataa ccgattagaa     180
aaaggcggat atgcccggga agtgacagta cgtgaattgc cgatttcaga aaaccttgca     240
tccgtaaata tgcggctgaa gccaggcgcg attcgcgagc ttcactggca taaagaagct     300
gaatgggctt atatgattta cggaagtgca agagtcacaa ttgtagatga aaaagggcgc     360
agctttattg acgatgtagg tgaaggagac ctttggtact tcccgtcagg cctgccgcac     420
tccatccaag cgctggagga gggagctgag ttcctgctcg tgtttgacga tggatcattc     480
tctgaaaaca gcacgttcca gctgacagat tggctggccc acactccaaa agaagtcatt     540
gctgcgaact tcggcgtgac aaaagaagag atttccaatt tgcctggcaa agaaaaatat     600
atatttgaaa accaacttcc tggcagttta aaagatgata ttgtggaagg gccgaatggc     660
gaagtgcctt atccatttac ttaccgcctt cttgaacaag agccgatcga atctgaggga     720
ggaaaagtat acattgcaga ttcgacaaac ttcaaagtgt ctaaaaccat cgcatcagcg     780
ctcgtaacag tagaacccgg cgccatgaga gaactgcact ggcacccgaa tacccacgaa     840
```

| | |
|---|---|
| tggcaatact acatctccgg taaagctaga atgaccgttt ttgcatctga cggccatgcc | 900 |
| agaacgttta attaccaagc cggtgatgtc ggatatgtac catttgcaat gggtcattac | 960 |
| gttgaaaaca tcggggatga accgcttgtc tttttagaaa tcttcaaaga cgaccattat | 1020 |
| gctgatgtat ctttaaacca atggcttgcc atgcttcctg aaacatttgt tcaagcgcac | 1080 |
| cttgacttgg gcaaagactt tactgatgtg ctttcaaaag aaaagcaccc agtagtgaaa | 1140 |
| aagaaatgca gtaaataa | 1158 |

```
<210> SEQ ID NO 2
<211> LENGTH: 249
<212> TYPE: DNA
<213> ORGANISM: Bacillus amiloliquefaciens

<400> SEQUENCE: 2
```

| | |
|---|---|
| gccccgcaca tacgaaaaga ctggctgaaa acattgagcc tttgatgact gatgatttgg | 60 |
| ctgaagaagt ggatcgattg tttgagaaaa gaagaagacc ataaaaatac cttgtctgtc | 120 |
| atcagacagg gtattttta tgctgtccag actgtccgct gtgtaaaaat aaggaataaa | 180 |
| ggggggttgt tattatttta ctgatatgta aaatataatt tgtataagaa aatgagaggg | 240 |
| agaggaaac | 249 |

```
<210> SEQ ID NO 3
<211> LENGTH: 180
<212> TYPE: DNA
<213> ORGANISM: Bacillus amiloliquefaciens

<400> SEQUENCE: 3
```

| | |
|---|---|
| tggatcgatt gtttgagaaa agaagaagac cataaaaata ccttgtctgt catcagacag | 60 |
| ggtattttt atgctgtcca gactgtccgc tgtgtaaaaa taaggaataa agggggggttg | 120 |
| ttattatttt actgatatgt aaaatataat ttgtataaga aatgagagg gagaggaaac | 180 |

```
<210> SEQ ID NO 4
<211> LENGTH: 181
<212> TYPE: DNA
<213> ORGANISM: Bacillus amiloliquefaciens

<400> SEQUENCE: 4
```

| | |
|---|---|
| tggatcgatt gtttgagaaa agaagaagac cataaaaata ccttgtctgt catcagacag | 60 |
| ggtatttttt atgctgtcca gactgtccgc tgtgtaaaaa aataggaata aaggggggtt | 120 |
| gttattattt tactgatatg taaaatataa tttgtataag aaaatgagag ggagaggaaa | 180 |
| c | 181 |

```
<210> SEQ ID NO 5
<211> LENGTH: 411
<212> TYPE: DNA
<213> ORGANISM: Bacillus subtilis

<400> SEQUENCE: 5
```

| | |
|---|---|
| gtgaaacatc aaaacccttc aaaacgctta ttgcggctct ccataaagta cttgctggcc | 60 |
| gcagcagcag tggtgttgac ctattttgct gtcatctata tattgttttc tttagcggga | 120 |
| acgagctacc gctcagcagc tcatgtcctg cttttttgccg tggtattcct tgttctcgga | 180 |
| ttatgctttg aaccatttga acggctgatg atacatagct ttacattttt caagacagga | 240 |
| aaacgtctat tcattctcct tgctggcatc gtacagctgc tgtttttgtg gatgactgct | 300 |
| catacaacag accaattgat cagcgacatc tggctgtcca ccacagaaga aatgattgtc | 360 |

```
gcagccgttt ttttgatttt agacaaatgc aactcggctc ttcccagcta a        411
```

```
<210> SEQ ID NO 6
<211> LENGTH: 33
<212> TYPE: DNA
<213> ORGANISM: Artificial
<220> FEATURE:
<223> OTHER INFORMATION: primer

<400> SEQUENCE: 6
ggctctagat tatttactgc atttcttttt cac                            33

<210> SEQ ID NO 7
<211> LENGTH: 36
<212> TYPE: DNA
<213> ORGANISM: Artificial
<220> FEATURE:
<223> OTHER INFORMATION: primer

<400> SEQUENCE: 7
agggagagga acatgaaaaa aacaaaatga cattcc                         36

<210> SEQ ID NO 8
<211> LENGTH: 36
<212> TYPE: DNA
<213> ORGANISM: Artificial
<220> FEATURE:
<223> OTHER INFORMATION: primer

<400> SEQUENCE: 8
gtcattttgt tttttcatag ctgtttcctg tgtgaa                         36

<210> SEQ ID NO 9
<211> LENGTH: 27
<212> TYPE: DNA
<213> ORGANISM: Artificial
<220> FEATURE:
<223> OTHER INFORMATION: primer

<400> SEQUENCE: 9
cgccgaattc tggatcgatt gtttgag                                   27

<210> SEQ ID NO 10
<211> LENGTH: 40
<212> TYPE: DNA
<213> ORGANISM: Artificial
<220> FEATURE:
<223> OTHER INFORMATION: primer

<400> SEQUENCE: 10
gtcattttgt tttttcatgt ttcctctccc tctcattttc                     40

<210> SEQ ID NO 11
<211> LENGTH: 24
<212> TYPE: DNA
<213> ORGANISM: Artificial
<220> FEATURE:
<223> OTHER INFORMATION: primer

<400> SEQUENCE: 11
cttttgctca catgttcttt cctg                                      24

<210> SEQ ID NO 12
<211> LENGTH: 36
<212> TYPE: DNA
<213> ORGANISM: Artificial
<220> FEATURE:
```

<210> SEQ ID NO 13
<211> LENGTH: 30
<212> TYPE: DNA
<213> ORGANISM: Artificial
<220> FEATURE:
<223> OTHER INFORMATION: primer

<400> SEQUENCE: 12
ttcacacagg aaacagctat gaaaaaacaa aatgac                36

<210> SEQ ID NO 13
<211> LENGTH: 30
<212> TYPE: DNA
<213> ORGANISM: Artificial
<220> FEATURE:
<223> OTHER INFORMATION: primer

<400> SEQUENCE: 13
ttatctagag cttgcttccg tctatcaagg                30

<210> SEQ ID NO 14
<211> LENGTH: 27
<212> TYPE: DNA
<213> ORGANISM: Artificial
<220> FEATURE:
<223> OTHER INFORMATION: primer

<400> SEQUENCE: 14
cttaagcttt ggatcgattg tttgaga                27

<210> SEQ ID NO 15
<211> LENGTH: 385
<212> TYPE: PRT
<213> ORGANISM: Bacillus subtilis

<400> SEQUENCE: 15

```
Met Lys Lys Gln Asn Asp Ile Pro Gln Pro Ile Arg Gly Asp Lys Gly
 1               5                  10                  15

Ala Thr Val Lys Ile Pro Arg Asn Ile Glu Arg Asp Arg Gln Asn Pro
            20                  25                  30

Asp Met Leu Val Pro Pro Glu Thr Asp His Gly Thr Val Ser Asn Met
        35                  40                  45

Lys Phe Ser Phe Ser Asp Thr His Asn Arg Leu Glu Lys Gly Gly Tyr
    50                  55                  60

Ala Arg Glu Val Thr Val Arg Glu Leu Pro Ile Ser Glu Asn Leu Ala
65                  70                  75                  80

Ser Val Asn Met Arg Leu Lys Pro Gly Ala Ile Arg Glu Leu His Trp
                85                  90                  95

His Lys Glu Ala Glu Trp Ala Tyr Met Ile Tyr Gly Ser Ala Arg Val
            100                 105                 110

Thr Ile Val Asp Glu Lys Gly Arg Ser Phe Ile Asp Asp Val Gly Glu
        115                 120                 125

Gly Asp Leu Trp Tyr Phe Pro Ser Gly Leu Pro His Ser Ile Gln Ala
    130                 135                 140

Leu Glu Glu Gly Ala Glu Phe Leu Leu Val Phe Asp Asp Gly Ser Phe
145                 150                 155                 160

Ser Glu Asn Ser Thr Phe Gln Leu Thr Asp Trp Leu Ala His Thr Pro
                165                 170                 175

Lys Glu Val Ile Ala Ala Asn Phe Gly Val Thr Lys Glu Glu Ile Ser
            180                 185                 190

Asn Leu Pro Gly Lys Glu Lys Tyr Ile Phe Glu Asn Gln Leu Pro Gly
        195                 200                 205

Ser Leu Lys Asp Asp Ile Val Glu Gly Pro Asn Gly Glu Val Pro Tyr
    210                 215                 220
```

-continued

```
Pro Phe Thr Tyr Arg Leu Leu Glu Gln Glu Pro Ile Glu Ser Glu Gly
225                 230                 235                 240

Gly Lys Val Tyr Ile Ala Asp Ser Thr Asn Phe Lys Val Ser Lys Thr
            245                 250                 255

Ile Ala Ser Ala Leu Val Thr Val Glu Pro Gly Ala Met Arg Glu Leu
        260                 265                 270

His Trp His Pro Asn Thr His Glu Trp Gln Tyr Tyr Ile Ser Gly Lys
    275                 280                 285

Ala Arg Met Thr Val Phe Ala Ser Asp Gly His Ala Arg Thr Phe Asn
290                 295                 300

Tyr Gln Ala Gly Asp Val Gly Tyr Val Pro Phe Ala Met Gly His Tyr
305                 310                 315                 320

Val Glu Asn Ile Gly Asp Glu Pro Leu Val Phe Leu Glu Ile Phe Lys
            325                 330                 335

Asp Asp His Tyr Ala Asp Val Ser Leu Asn Gln Trp Leu Ala Met Leu
        340                 345                 350

Pro Glu Thr Phe Val Gln Ala His Leu Asp Leu Gly Lys Asp Phe Thr
    355                 360                 365

Asp Val Leu Ser Lys Glu Lys His Pro Val Val Lys Lys Lys Cys Ser
370                 375                 380

Lys
385

<210> SEQ ID NO 16
<211> LENGTH: 1730
<212> TYPE: DNA
<213> ORGANISM: Bacillus subtilis

<400> SEQUENCE: 16
atgaaaaaac aaaatgacat tccgcagcca attagaggag acaaaggagc aacggtaaaa      60
atcccgcgca atattgaaag agaccggcaa aaccctgata tgctcgttcc gcctgaaacc     120
gatcatggca ccgtcagcaa tatgaagttt tcattctctg atactcataa ccgattagaa     180
aaaggcggat atgcccggga agtgacagta cgtgaattgc cgatttcaga aaaccttgca     240
tccgtaaata tgcggctgaa gccaggcgcg attcgcgagc ttcactggca taagaagct      300 gaatgggctt atatgattta cggaagtgca agagtcacaa ttgtagatga aaagggcgc      360 agctttattg acgatgtagg tgaaggagac ctttggtact tcccgtcagg cctgccgcac     420
tccatccaag cgctggagga gggagctgag ttcctgctcg tgtttgacga tggatcattc     480
tctgaaaaca gcacgttcca gctgacagat tggctggccc acactccaaa agaagtcatt     540
gctgcgaact cggcgtgac aaaagaagag atttccaatt tgcctggcaa agaaaaatat     600
atatttgaaa ccaacttcc tggcagttta aaagatgata ttgtggaagg ccgaatggc      660 gaagtgcctt atccatttac ttaccgcctt cttgaacaag agccgatcga atctgaggga     720
ggaaaagtat acattgcaga ttcgacaaac ttcaaagtgt ctaaaaccat cgcatcagcg     780
ctcgtaacag tagaacccgg cgccatgaga gaactgcact ggcacccgaa tacccacgaa     840
tggcaatact acatctccgg taagctaga atgaccgttt ttgcatctga cggccatgcc     900
agaacgttta attaccaagc cggtgatgtc ggatatgtac catttgcaat gggtcattac     960
gttgaaaaca tcggggatga accgcttgtc tttttagaaa tcttcaaaga cgaccattat    1020
gctgatgtat ctttaaacca atggcttgcc atgcttcctg aaacatttgt tcaagcgcac    1080
cttgacttgg gcaaagactt tactgatgtg ctttcaaaag aaaagcaccc agtagtgaaa    1140
aagaaatgca gtaaataaaa gacttgccgc ttgcagagag cactcgttct ctgcaagcct    1200
```

-continued

| | |
|---|---|
| tcataaggag ctgaaccagt gaaacatcaa aaccccttcaa aacgcttatt gcggctctcc | 1260 |
| ataaagtact tgctggccgc agcagcagtg gtgttgacct attttgctgt catctatata | 1320 |
| ttgttttctt tagcgggaac gagctaccgc tcagcagctc atgtcctgct ttttgccgtg | 1380 |
| gtattccttg ttctcggatt atgctttgaa ccatttgaac ggctgatgat acatagcttt | 1440 |
| acattttca agacaggaaa acgtctattc attctccttg ctggcatcgt acagctgctg | 1500 |
| tttttgtgga tgactgctca tacaacagac caattgatca gcgacatctg gctgtccacc | 1560 |
| acagaagaaa tgattgtcgc agccgttttt ttgattttag acaaatgcaa ctcggctctt | 1620 |
| cccagctaaa aaagaacgc attccaattg gatgcgttct ttttattcat agcgaagcgc | 1680 |
| gtctacaggc tgaagcttcg aagccttgat agacggaagc aagccgaaga | 1730 |

<210> SEQ ID NO 17
<211> LENGTH: 1155
<212> TYPE: DNA
<213> ORGANISM: Bacillus licheniformis

<400> SEQUENCE: 17

| | |
|---|---|
| atggaaaaaa acaaacaaat tccacagccg atcagaggag aaaaaggagc ggaaacgaaa | 60 |
| attccgcaca acgttgagcg cgaccgccaa aacccggaca tgctcgtacc gcctgaaacc | 120 |
| gaccacgaa cggtgccaaa catgaaattt tcattttccg atgtccataa ccgtcttgaa | 180 |
| aaaggcggat atgcacggga agtcacagtt cgcgagctgc cgatttcaga caagcttgct | 240 |
| tctgtcaaca tgaggctgaa acctggggcc atcaggagc tgcactggca taaggaagcc | 300 |
| gaatgggcgt atatgctgta cggaaaagca cggattacgt ctgttgacca agacggcaga | 360 |
| aactttattg aagatgtgaa agaaggagat ctctggtact tcccgtcagg tctgccgcat | 420 |
| tcaattcaag cacttgaaga cggatgcgaa ttcctgcttg tcttcgatga cggctccttc | 480 |
| tctgaaaaca gcaccttcca ggtgacagat tggctggccc atacgcctga tgaggtgatt | 540 |
| gccgcaaact tcggcatttc aaaagacgtc gtcgcctctc ttccagttga agaaaagtat | 600 |
| attttccaag aagcgatccc tggctgtctt gagaaagaca agttgaaag cccgaacgga | 660 |
| acggtacctc tatctttcag ctacaatttg cttgaacagg aaccgattat atccatcgga | 720 |
| ggaaaagtat ggattgccga ttccacgaac ttcaaagcat cgaaaacgat cgcttctgcg | 780 |
| ttagtggaag tcgaacctgg aggcatccgg gagctgcact ggcatccgaa tacagacgaa | 840 |
| tggcagtatt acatttccgg acaagcgaaa atgacggttt tcgctgccga cgggcatgcc | 900 |
| agaacattta attaccaggc cggagatgtc ggctatgtgc cgttcgcaat gggacactac | 960 |
| gtccaaaata caggagatga gccgcttcgg ttcctcgaaa ttttcaaaga cgaccactat | 1020 |
| gctgacgttt cgttaaacca atggctcgcg cttgttccgg aagagcttgt ccgccagcac | 1080 |
| cttgacgtcg gcagcgaatt tacaaaaatg ctctctaaag aaaagcatcc ggtcgtcaaa | 1140 |
| tttgataaga aataa | 1155 |

<210> SEQ ID NO 18
<211> LENGTH: 2662
<212> TYPE: DNA
<213> ORGANISM: Flammulina velutipes

<400> SEQUENCE: 18

| | |
|---|---|
| atccatcgca tttccgatgt tcaacaactt ccaacgtctg ctcactgtca tccttctctc | 60 |
| cggttttacc gctggagtgc ctttggcgtc caccacgacg ggaactggaa ctgcgaccgg | 120 |
| tacctcaacc gccgcagagc ccagcgcgac tgtccccttc gccagcactg atcccaaccc | 180 |

```
cgtgctctgg aatgagacca gtgacccagc gcttgtaaag ccagagagga accagcttgg    240
tgcgacaatc caaggaccgg ataatctgcc tatagacctt cagaatccgg acttgctcgc    300
cccaccgact actgatcatg gctttgtgtg agttttttgta tactagtact ggctgggtat    360
gtgattgaag aggttttaca gcggtaatgc gaagtggcca ttcagcttca gcaagcagcg    420
actgcagacg ggtggctggg ctcggcagca gaatggtggg ttgtcttcgt tgatttgggg    480
tgctttggac gctgacggat cgttcaagag gtcgttttgc ctctcgcgac tagtaagcta    540
aacctttact tagcttggtc gacaaagcat aaacatatcg aacagatctc gcttgcacaa    600
atatgcgtct tgaagcaggc gctatcaggt actatggttc gcatcctgtc gcgtcaagag    660
tttgaccgct ctttcttaca cagggagctg cattggcaca agaacgctga ggtacgtctg    720
tctgacccag tcaatgtttt cttcgaactt agactttccc tagtgggcat atgttctgaa    780
ggtgctgaaa actgtgtatg caatttcgtc gtgagactga gaatatcgtc atagggtct    840 acccaaatct cagctgtcga taacgaaggg cgcaattata tttccaccgt cgtgagtgta    900
cttgcacata tactttatta gacttattta ctgtgaccga cttttagggc cctggtgatt    960
tgtggtactt cccaccaggc attcctcact cgctacaagc gacagccgat gatccagaag   1020
gctcagagtt catcttagta tgcattactc attctttgtg gtcatgacaa gtggctgaag   1080
aaagtctttt tgcgaaggtc tttgattcag gcgccttcaa tgacgacggt acattcttgg   1140
tatgagatct ctctctttcc tacgtgtcat agaactcaac atattcagct cactgactgg   1200 cttttcgcatg ttcaatgga aggtcggcca acccactttg atcaagtatt ggtatactaa   1260
gagctcgact actttgtagt tatcctgaag aacttcagag ccaagaatcc gccgcatgg    1320 tctcacatac ctgctcaaca gctatacatc ttccctagtg gtgcgtttcc tcttcctctt   1380
cccctgaccg tgacacggct caacatgtaa catagaacct cctgcggaca accagccgga   1440
ccccgttagc ccacagggga cggttcccct tccatattca ttcaacttct cctctgtcga   1500
gccgacgcag tattccggtg ggacagcgaa gattgcagat tccacgacgt tcaacatttc   1560
cgtcgctatc gccgtggccg aggttacagt tgagcctggt gctttgaggt gggtttctcg   1620
tagtggcttt gcacgttcta aatctgaccc ttggtatcaa gagagctgca ctggcatccg   1680
actgaggacg agtggacatt cttcatgtat gtgtactttc ggagatgcca agatgtataa   1740
taactcggtt tacagctctg gaaacgcgag ggtgacaatt ttcgctgcgc agagtgtagc   1800
ctctacgttt gattaccaag gtggtgatat cggtgagtac atttagtctg agcgaagtgc   1860
ttagtgaagc tgactgccga cagcttatgt tcctgcatct atgggtacca tttatcttc    1920 ctccatcttg cctgaatctt ttctgacatc ttttactaca ggccattatg tagagaacat   1980
tggaaacacg actttgactt atctggaggt cttcaatacc ggtgcgttat acaacaatgc   2040
gcgttgttct tctgctcatg tgtatcatgc agaccgtttt gctgatgtca gtctaagtca   2100
ggtatgtttg ttgtagcata tacggagtta tatactgagc gagtgcacag tggctggcgt   2160
taacacctcc gagtgtcgtg caggcgcacc tgaacttgga cgacgagaca cttgcggagc   2220
tcaagcagtt tgcgaccaag gcgactgttg ttggtcctgt gaactgaact ttcgttcctt   2280
taaactcatc aaattatcat tggaattcta tgtagatgtt gtaatcaatg cagttcttcg   2340
gctatcccgt tgaagaggat attgatgata aggcattatg ggcaagttca ttattcgaat   2400
aaacttaact gagatcagcc tcgctgcaac ggagcggttt ccttttacgg ccggatatga   2460
tttcctcccg gccggtcgct tgttcctctc cctccatcct ttggctaggg cacattctcg   2520
ttccacgtat ggtggttgta ttggactttg gcgaggaccg tagcaagttc aaggccttg    2580
```

| | |
|---|---:|
| attacaccta caccottgat gtcactaatt gccgcgagtt gactctggaa gcgatagacg | 2640 |
| ttagcccgac acgataccct ca | 2662 |

<210> SEQ ID NO 19
<211> LENGTH: 1197
<212> TYPE: DNA
<213> ORGANISM: Bacillus cereus

<400> SEQUENCE: 19

| | |
|---|---:|
| atgaagaaac gtactgttaa tgaagcagga aggaatgtgc cacaaccaat ccgcagcgac | 60 |
| ggagcaggtg cgattgattc tggacctcgt aatgttatgc gggatattca aaatccgaat | 120 |
| atgcttgttc cgcctataac ggatgcaggg ttagttccta acttgaagtt ttcattctcg | 180 |
| gacacttcta tgattttgaa acaaggcggg tggtctcggg agattactgc tcgggaacta | 240 |
| ccggtttcga cgacgattgc cggagtaaat atgagtttaa cggcaggtgg agtacgagaa | 300 |
| ctacattggc ataaagaagc agaatgggcg tatatgcttt taggacgggc acgcataacg | 360 |
| gctgtagatc aaaatggacg gaattttatt gctgatgttg gaccaggtga tctttggtat | 420 |
| tttcctcctg gtattccgca ttccattcaa ggattggaac attgtgaatt tctactcgtt | 480 |
| tttgatgatg ggcatttttc tgatttatct actttagcta tttctgattg gtttgcgcat | 540 |
| acgccaaaag aagtgttgtc ggctaatttt ggagtacctg agagtgtttt tcgttctctc | 600 |
| ccttcagatc aagtttatat ttatcaagga gaggtgccag gttcgcttga aagtcaggaa | 660 |
| gttcaatcac cgaaaggaga agttcccttta acatttaaac atgaattgtt aaaacaaaag | 720 |
| ccggttaaga cgcctggtgg tagcgttcga attgtagatt ctacaaattt ccctatttca | 780 |
| aaaacaatcg cagcagcgct tgttgaggtt gagcctggtg aatgagaga acttcattgg | 840 |
| caccccgaata atgatgaatg gcaatattat ttgacagggg aagcgagaat gactgtgttt | 900 |
| cttggaaatg gtaccgctcg tacatttgat tatagagctg gcgatgtcgg atatgtaccg | 960 |
| tttgcgacgg ggcattatat tcaaaataca ggtaccgaaa cattatggtt tttagagatg | 1020 |
| ttcagaagca atcgttttga agatgtatcg ttaaatcaat ggatggcact gactcctaaa | 1080 |
| gaaatagtgg agagtaatat acatgttggc ccgcaagtaa tggattctct gcgtaaggag | 1140 |
| aagtggcctg ttgtgaaata tccggggttt tcatatagtc gaaaagtga tgagtaa | 1197 |

<210> SEQ ID NO 20
<211> LENGTH: 1434
<212> TYPE: DNA
<213> ORGANISM: Aspergillus nidulans

<400> SEQUENCE: 20

| | |
|---|---:|
| atgaagtcca cccttgcact ttcactctcg ttctcacttc ttgagctcct gcctctcatc | 60 |
| catggagcac caacctttac caagcgacaa gacaccggcc cgaaccccc gctacgcgga | 120 |
| tcgaaagacc tgctcggcta ttcgccaaac aacaagctga cagagcagac cacagaggac | 180 |
| atccagtata cccttgttcc cggacagaca gaggacgaag atcttggtgt atacctggac | 240 |
| ttctcgaaca acccaaatcc gcagccgatc cgtggctcaa agggaggaac tgatcctggc | 300 |
| ccgcgtaacc cggagctcga ccgccagaac agcgacaagc tagctccgcc cggaacagac | 360 |
| catgacaga ctatcaatgc caactggccc atgtctctta gcaaagccaa gtgcgtgtca | 420 |
| agcagactcg gtctcgacca tgcaggatgg tcccggcaag agaacgtcgt cgttatgcct | 480 |
| gccgccacaa agatggccgg cgtagacatg cgtcttgaag ccagcgctta tcgtgagctg | 540 |
| cactggcacc aagctggcga gtggagtctg gttctcaacg ggtcgtgcag gattcaggct | 600 |

```
gtgaacgaag atggccagac cttcatcgac gacgtcacag agggcgatgt gtggttttt      660 cctcccggcg tcccacactc catacaagcc ctagatgtcg gcgtcgagtt cctcctcgtc     720
ttcgacgacg gctctttctc cgaagacaac accttcctcg cctccgagat cttcgcgcat     780
aacccgaaat ccgtcctcag caagaatttt gacctccccg tctctgcctt cgacgacatc     840
ccctccggcg aactctttat cttccctggc actgctccac ccacagaaat tgccgcccag     900
aacaaatcca ccgccgcagg gcctgtcccg cgcgaccgaa catactcgta ccacttctct     960
gagcagcccg cacatatcgt cccgggtggg agcgtcaaga tcgtggaccc ccaaaacttc    1020
cccgcggcca gtaacttcgc tgcagcagtg gtgaccgtta agcccggtgc aatgcgagag    1080
attcactggc acccaacaag cgacgagtgg agtttcttta tcaggggcca gggccgggcg    1140
acgcttattg aagcaccatc gacggcgacg acgtttgact tccatgctgg tgatgtggga    1200
tactttccta tgtcgcatag ccactatatc gagaatacag gggaagagga tctggtcttg    1260
cttgaggtgt tgcaagctga ccactttagt gatatcgctt taggccagtg gctcggctca    1320
acggataagc agatagtcgg tgatacgctg cgtttgcctg aggatgcgct caatcaattg    1380
aagtcagaaa agcagtatgt tgttgctgca ccgagcaatg ctacgcaagc gtga           1434
```

<210> SEQ ID NO 21
<211> LENGTH: 1185
<212> TYPE: DNA
<213> ORGANISM: Streptococcus mutans

<400> SEQUENCE: 21

```
atgacaacac ccaacacccc acagccgcaa agaaaaagcg acggaaaagg ttggcttgat       60
tttggaccgc gtaacttgag ccgcgataat gaaaatccgg atatcttggt tccgcctgtc      120
actgaccatg ggaccatgcc caatatgcgc tacagctttt cagatgccca caatcggatg      180
gaagaaggag gctgggcgcg tgaagtgacc attcgtgaac tgcctgcttc agatgaattg      240
gctggtgtca atatggcctt ggcaccaggt gcttatcgtg aactgcattg gcacaaagaa      300
gccgaatggg gacttatgct gtacggcaat gcccgcatta cagcgattga cgagaacggt      360
cagtcttata ttgatgatgt cgaagaagga gatctttgga attttgaatc cggcgttgct      420
cattctattc aggccttgga taagggctgt gagtttctgt tagttttcag cgaagccaat      480
ttctcagaga atcaaacctt actgcttagt gactggttgg ctcacactcc tgatgacatc      540
gttgctgcta attttaaaaa gaccgaggaa gaattggcta gtcttcctaa gacagaaaaa      600
tatatcttta atgggactat tcctggttct attgaagcag agaagcgcac caatcccaat      660
ggtgatgtgg tcaatccgct gacactgcat ttggataaaa ttgcaccgat tcagtcagaa      720
gctggacgtg cttggatttt ggatcagaag gtctttccgg ctgctaagac gatttcagca      780
gctattgttg aggttgagcc gggcggtatg cgggaattgc actggcatcc taagtcatcc      840
gaatggcagt attacatcaa gggtcaggcc cgcatgacga tttttaattc taatggtttg      900
gctcgtacct atgactttc agctggagat gtaggctatg tacccaatgt agcggggcat       960
tatgttcaaa atacgggtga cgaaacgttg gtcttcgttg aagtttttcg taaccctgat     1020
tattccgata tttcgctcaa taagtggctg gcgacaactc ctgtcaataa tgttgcagag    1080
cacctcaatc ttcctaagga acttgtccaa aatcttcctc aggcagagac tccgcaaccct    1140 gtcatttggt ttgataagga taaggctgca aaaaagcctt tttag                     1185
```

RECOMBINANT EXPRESSION PLASMID VECTOR AND RECOMBINANT STRAIN TO BE USED IN PRODUCING OXALATE DECARBOXYLASE, AND METHOD OF PRODUCING RECOMBINANT OXALATE DECARBOXYLASE

TECHNICAL FIELD

The present invention relates to an oxalate decarboxylase originating in microorganisms. Specifically, the present invention relates to a recombinant expression plasmid vector and a recombinant bacterium used in production of an oxalate decarboxylase, a preparation method of an oxalate decarboxylase producing bacterium and a production method of a recombinant oxalate decarboxylase.

BACKGROUND ART

Oxalic acid is a general compound that is contained in many foods (in particular, spinach and other deep green vegetables, green tea, cocoa, etc.), or generated in a human body (generated in a process of metabolism, not decomposed further more in a living body and excreted with urine). Oxalic acid has been well known as a substance to be a factor of stone due to combining with calcium in a human body. Further, increase of an oxalic acid concentration in urine (increase of risk of stone formation) has also been observed due to excess intake of oxalic acid and an overproduction of oxalic acid in a human body. Furthermore, oxalic acid has been utilized also as an attacking means of a phytopathogenic fungus to plants. That is, there has been known existence of a phytopathogenic fungus which makes an attack such that oxalic acid is produced in infected plant tissues, thereby making the insides of the plant tissues acidic environments to blight leaves.

As described above, although oxalic acid is a general compound, it is a compound showing a harmful effect on organisms. An enzyme that decomposes oxalic acid having such an effect is useful in various fields such as the food field and the medical field. For example, oxalic acid in foods is decomposed directly or after taking in a body with an enzyme or an oxalic acid decomposing bacterium, to thus try to decrease a concentration of oxalic acid absorbed in a body. In addition, it has been performed to introduce an oxalic acid degrading enzyme into a plant body for the purpose of imparting resistance against phytopathogenic fungi.

As an enzyme that decomposes oxalic acid, an oxalate decarboxylase (hereinafter also referred to as "OXDC"), an oxalate oxidase, and an oxalyl CoA decarboxylase have been known to exist. OXDC is an enzyme that decomposes oxalic acid into formic acid and carbon dioxide, and contains manganese in its inside. It has been revealed so far that many kinds of bacteria (such as genus *Bacillus*) and fungi (genus *Aspergillus*, and *Flammulina velutipes*) have oxalate decarboxylase genes (hereinafter also referred to as "oxdc gene"). There have been trials to find out enzymological properties of OXDC, in particular, clarification of OXDC of *Bacillus subtilis* and *Flammulina velutipes* has progressed.

It has been reported on OXDC originating in the genus *Bacillus* that OXDC productivity of a *Bacillus subtilis* 168 strain that is a general producing bacterium is 0.4 mg/L in a culture liquid (Non-patent Document 1). An oxdc gene is cloned using *Escherichia coli* as a host for the purpose of clarification of enzymological properties (Non-patent Document 2). The oxdc gene recombinant *Escherichia coli* has higher productivity than a *Bacillus subtilis* 168 wild strain does, and shows OXDC productivity of 2.8 mg per 1 g of cultured bacterial bodies. However, even though this productivity is sufficient at a laboratory level, it cannot be recognized as being sufficient at a practical and commercial level.

[Non-patent Document 1] J. Bacteriol. 182 (2000), 5271-5273

[Non-patent Document 2] J. Biol. Chem. 276 (2001), 43627-43634

DISCLOSURE OF THE INVENTION

Problems to be Solved by the Invention

In view of the above-described backgrounds, an object of the present invention is to provide a means for highly producing an oxalate decarboxylase originating in a microorganism. Specifically, an object is to provide an expression plasmid vector useful for preparation of a recombinant bacterium highly producing the oxalate decarboxylase originating in a microorganism, a recombinant bacterium prepared using the vector, and an oxalate decarboxylase producing system using the recombinant bacterium.

Means for Solving the Problems

The present inventors have repeated studies for the purpose of finding out a method for highly producing OXDC originating in a microorganism. Specifically, using OXDC originating in the genus *Bacillus* as a typical example of OXDC originating in a microorganism, construction of its high production system was tried. First, the inventors focused on an α-amylase promoter belonging to the genus *Bacillus*, and prepared a recombinant expression plasmid vector ligated with an oxdc gene under the control of the promoter. Then, recombinant bacteria (*Bacillus subtilis* and *Escherichia coli*) transformed with the vector were obtained. As a result of the investigation on the productivity of the recombinant bacteria, significant improvement in productivity was recognized as compared to the past reports (Non-patent Documents 1 and 2). It was also revealed that in the case of using a promoter in which 3 sites are mutated (mutated promoter) as the promoter, further improvement in productivity was achieved. What is more, high productivity was recognized also in a recombinant bacterium obtained by transforming with an expression plasmid vector ligated with a yvrL gene in addition to an oxdc gene. On the other hand, culture conditions in a production system where *Bacillus subtilis* and *Escherichia coli* were used as hosts were studied and a range of a manganese (Mn) concentration to enhance productivity was determined.

As described above, the inventors obtained a finding that an α-amylase promoter originating in the genus *Bacillus* is useful for constructing a high production system of OXDC originating in a microorganism and, at the same time, succeeded in finding out a mutated promoter particularly useful for improvement in productivity. Further, they obtained such a finding that high productivity was attained also when an oxdc gene ligated with a yvrL gene is used. What is more, the inventors also succeeded in finding out culture conditions to enhance productivity.

The present invention is based on these achievements and provides the list in the following; a recombinant expression plasmid vector, a preparation method of an oxalate decarboxylase producing bacterium, a recombinant bacterium (recombinant oxalate decarboxylase producing bacterium), and a production method of a recombinant oxalate decarboxylase.

[1] A recombinant expression plasmid vector, containing an α-amylase promoter belonging to the genus *Bacillus* and an oxalate decarboxylase gene originating in a microorganism that is provided under the control of the promoter.

[2] The recombinant expression plasmid vector according to [1], wherein the α-amylase promoter is a promoter originating in *Bacillus amyloliquefaciens*.

[3] The recombinant expression plasmid vector according to [1], wherein the α-amylase promoter has a DNA sequence set forth in any one of the SEQ ID Nos. 2 to 4.

[4] The recombinant expression plasmid vector according to any one of [1] to [3], wherein the microorganism is a bacterium belonging to the genus *Bacillus*.

[5] The recombinant expression plasmid vector according to any one of [1] to [3], wherein the microorganism is *Bacillus subtilis*.

[6] The recombinant expression plasmid vector according to any one of [1] to [3], wherein the microorganism is a *Bacillus subtilis* 168 strain.

[7] The recombinant expression plasmid vector according to any one of [1] to [3], wherein the oxalate decarboxylase gene originating in a microorganism has a DNA sequence set forth in the SEQ ID No. 1.

[8] The recombinant expression plasmid vector according to any one of [1] to [7], containing a yvrL gene downstream of the oxalate decarboxylase gene originating in a microorganism.

[9] The recombinant expression plasmid vector according to [8], wherein the yvrL gene contains a DNA sequence set forth in the SEQ ID No. 5.

[10] The recombinant expression plasmid vector according to [8], containing a DNA fragment of a sequence set forth in the SEQ ID No. 16.

[11] A method for preparing an oxalate decarboxylase producing bacterium, wherein a host bacterium is transformed with the recombinant expression plasmid vector according to any one of [1] to [10].

[12] The preparation method according to [11], wherein the host bacterium is *Escherichia coli* or a bacterium belonging to the genus *Bacillus*.

[13] A recombinant bacterium, which is obtained by transforming *Escherichia coli* or a bacterium belonging to the genus *Bacillus* with the recombinant expression plasmid vector according to any one of [1] to [10].

[14] The recombinant bacterium according to [13], wherein the bacterium belonging to the genus *Bacillus* is *Bacillus subtilis*.

[15] The recombinant bacterium according to [13], wherein the bacterium belonging to the genus *Bacillus* is a *Bacillus subtilis* 168 strain.

[16] A method for producing a recombinant oxalate decarboxylase, including:
a step of culturing the recombinant bacterium according to any one of [13] to [15]; and
a step of recovering the oxalate decarboxylase thus produced.

[17] A method for producing a recombinant oxalate decarboxylase, including:
a step of culturing a recombinant bacterium obtained by transforming *Escherichia coli* with the recombinant expression plasmid vector according to any one of [1] to [10] in a medium having a manganese concentration of 1 mM to 5 mM; and
a step of recovering the oxalate decarboxylase thus produced.

[18] A method for producing a recombinant oxalate decarboxylase, including:
a step of culturing a recombinant bacterium obtained by transforming a bacterium belonging to the genus *Bacillus* with the recombinant expression plasmid vector according to any one of [1] to [10] in a medium having a manganese concentration of 0.1 mM to 1 mM; and
a step of recovering the oxalate decarboxylase thus produced.

BRIEF DESCRIPTION OF DRAWINGS

FIG. 1 is a table showing combinations of hosts and promoters.

FIG. 13 is a table of comparing OXDC productivity among recombinant bacteria.

BEST MODE FOR CARRYING OUT THE INVENTION

Recombinant Plasmid Vector

Figure 2:
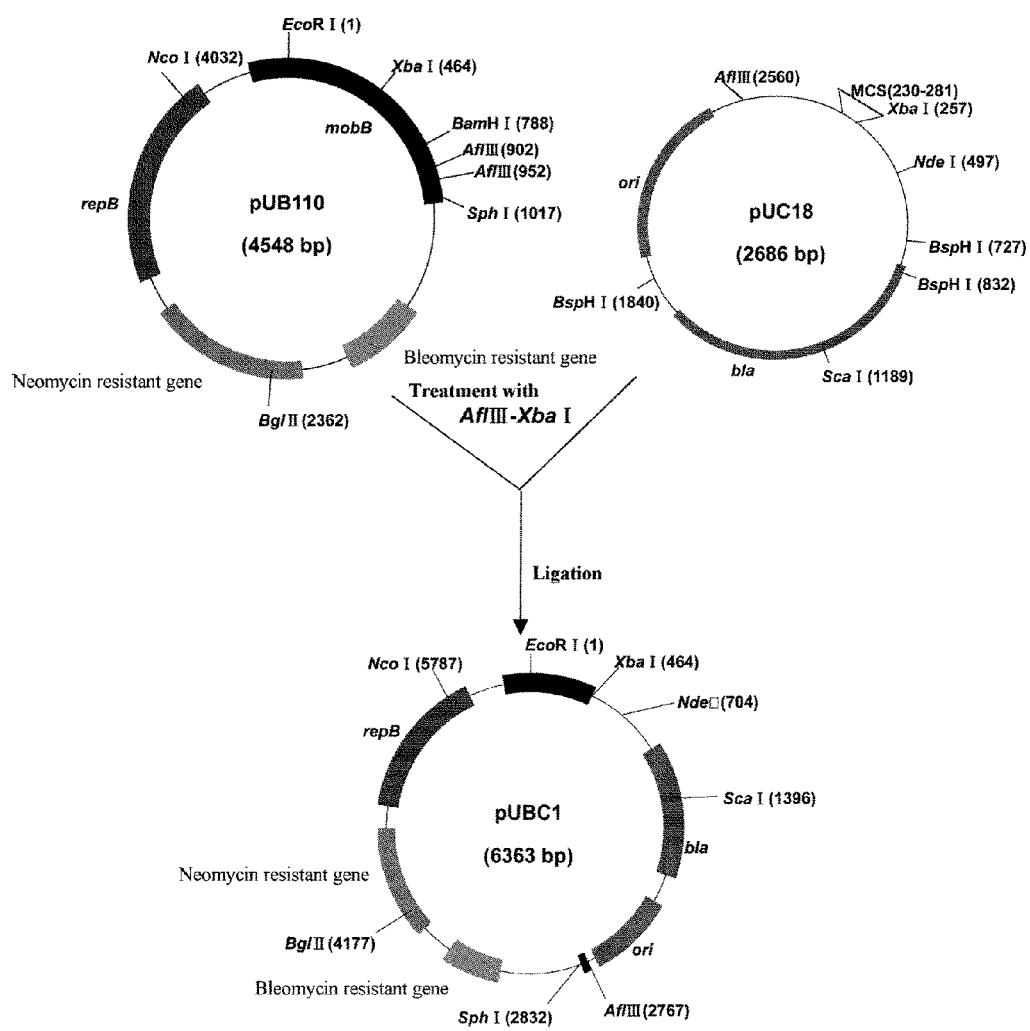
FIG. 2 illustrates a production procedure of shuttle vector pUBC1.

The first aspect of the present invention relates to a recombinant expression plasmid vector (hereinafter, also referred to as "expression vector"). "Recombinant" means that the expression plasmid vector is not naturally present, but is obtained as a result of an artificial operation with a genetic engineering technique.

In the expression vector of the present invention, an oxalate decarboxylase gene originating in a microorganism (oxdc gene originating in a microorganism) was arranged under the control of an α-amylase promoter belonging to the genus *Bacillus*. In addition, "an oxalate decarboxylase gene (oxdc gene)" is referred to as a DNA region (so-called structure gene) that encodes an amino acid sequence of an oxalate decarboxylase as otherwise particularly mentioned, and does not contain an regulatory region such as a promoter.

The "promoter" is referred to as a function region that regulates initiation of transcription of a gene under its control.

The promoter of the present invention is not particularly limited as long as it is an α-amylase promoter originating in the genus *Bacillus*. Examples of "the genus *Bacillus*" referred herein include *Bacillus amyloliquefacien, Bacillus subtilis, Bacillus licheniformis, Bacillus stearothermophilus* and *Bacillus thuringiensis*, and preferably *Bacillus amyloliquefaciens*. A DNA sequence of an α-amylase promoter of *Bacillus amyloliquefaciens* is set forth in the SEQ ID No. 2 (region from 1st base to 249th base of GenBank Accession No. J01542). In one embodiment of the present invention, an α-amylase promoter constituted with the DNA sequence is used. A part of the promoter can also be used as long as it has a promoter activity. For one example, a DNA sequence set forth in the SEQ ID No. 3 (DNA sequence obtained by deleting 69 bases in 5' side of the DNA sequence of the SEQ ID No. 2) is shown. When this promoter is used, a preferable promoter activity is observed (see section of Examples described later). When a variant (SEQ ID No. 4) of the promoter (SEQ ID No. 3) is used, a more preferable promoter activity is observed (the DNA sequence of SEQ ID No. 4 is a variant of the DNA sequence of SEQ ID No. 3 having 3 different sites (insertion of 1 base between 100th base and 101st base, substitution of 101st base and 102nd base)). As supported by this fact, even with a DNA sequence obtained by modifying a part of the DNA sequence set forth in the SEQ ID No. 3, there are cases where the DNA sequence keeps or improves the promoter activity. Thus, a promoter made of a DNA sequence that is partially different form the DNA sequence set forth in the SEQ ID No. 3 may be used, as long as it exerts a promoter activity. That is, even a DNA fragment made of a DNA sequence containing substitution, deletion, insertion, addition or inversion of one or plural bases based on the DNA sequence set forth in the SEQ ID No. 3 may be used as the promoter of the present invention, as long as it exerts a promoter activity. Substitution or deletion of bases may occur in plural sites. "Plural" herein indicates, for example, 2 to 40 bases, preferably 2 to 20 bases, and more preferably 2 to 10 bases.

"Under the control" has the same definition of "under the dominion", and means that a promoter and a structure gene is functionally connected. Transcription of the structure gene receives control (regulation) of the promoter by arranging the structure gene under the control of the promoter. Typically, the structure gene is directly connected to the promoter, but as long as the structure gene is controlled in transcription by the promoter, another sequence may be present between the promoter and the structure gene.

An α-amylase promoter originating in the genus *Bacillus* can be prepared using a standard genetic engineering technique, molecular biological technique, biochemical technique, or the like, in reference to sequence information disclosed in the present specification or attached sequence listings, or sequence information registered in public database (for example, DDBJ/EMBL/GenBank). For example, a desired promoter can be prepared through a series of operations of preparation of a chromosome DNA of a bacterium belonging to the genus *Bacillus*, amplification of a promoter region with a specific primer, and recovery of the amplified product. The specific primer can be easily synthesized using a commercially available automated DNA synthesizer, or the like. For amplification of a promoter region, PCR is preferably performed, for example.

In the expression vector of the present invention, an oxdc gene originating in a microorganism is arranged under the control of the promoter. It has been revealed that various microorganisms have oxdc genes, and some of the genes were identified in their sequences and functional analyses thereof were also performed. Examples of oxdc genes originating in microorganisms that are registered in public database are shown below (name of microorganism: name of database: registration No.: SEQ ID No. in sequence listing).

*Bacillus subtilis*: GenBank: Z99120: SEQ ID No. 1
*Bacillus licheniformis*: GenBank: CP000002: SEQ ID No. 17
*Flammulina velutipes*: GenBank: AF200683: SEQ ID No. 18
*Bacillus cereus*: GenBank: AE016877: SEQ ID No. 19
*Aspergillus nidulans*: GenBank: AACD01000139: SEQ ID No. 20
*Streptococcus mutans*: GenBank: AE014133: SEQ ID No. 21

The most significant characteristic of the present invention lies in using an α-amylase promoter originating in the genus *Bacillus* and an oxdc gene originating in a microorganism in combination, and species of the oxdc gene originating in a microorganism is not particularly specified. Therefore, any of oxdc genes originating in microorganisms, which have been identified so far, may be employed in principle. An oxdc gene belonging to the genus *Bacillus* is preferably used. An oxdc gene of *Bacillus subtilis* set forth in the SEQ ID No. 1 is particularly preferably used.

For example, an oxdc gene originating in a microorganism used in the expression vector of the present invention is prepared by preparing a chromosome DNA of a microorganism having the oxdc gene, thereafter isolating the oxdc gene utilizing a sequence specific probe or primer. For example, a preparation method of a chromosome DNA of a bacterium belonging to the genus *Bacillus* is specifically described in Molecular Biological Methods for *Bacillus*, John Wiley & Sons Ltd (1990), etc. Additionally, a method of isolating a desired DNA can be referred to Molecular Cloning (Third Edition, Cold Spring Harbor Laboratory Press, New York), Current protocols in molecular biology (edited by Frederick M. Ausubel et al., 1987), etc.

A terminator (transcription termination sequence) may be connected downstream of an oxdc gene. An α-amylase terminator, a T7 terminator, an fd phage terminator, a T4 terminator, and the like may be used as the terminator, other than the original terminator.

In consideration of condensation of codons, a gene having a DNA sequence encoding the same protein (that is, OXDC) is functionally equivalent to the DNA sequence set forth in the SEQ ID No. 1, and can be used as the oxdc gene in the present invention. Further, in general, when a part of an amino acid sequence of a protein is modified, the protein after modification may have the same function as that of the protein before alteration in some cases. That is, modification of an amino acid sequence does not give substantial effects on a function of a protein, and the function of the protein may be kept before and after the modification in some cases. Thus, a DNA sequence having an amino acid sequence homologous to a protein (the amino acid sequence is set forth in the SEQ ID No. 15) that the DNA sequence set forth in the SEQ ID No. 1 encodes and encoding a protein that functions as an oxalate decarboxylase (hereinafter also referred to as a "homologous protein") can also be used as the oxdc gene of the present invention. The "homologous amino acid sequence" herein refers to an amino acid sequence that differs in a part in an amino acid sequence set forth in the SEQ ID No. 15 but does not give a substantial effect on a function (OXDC activity in this case) of a protein due to the difference.

"The partial difference in an amino acid sequence" typically refers to occurrence of mutation (change) in an amino acid sequence due to deletion and substitution of 1 to several amino acids constituting the amino acid sequence, or addition and insertion of 1 to several amino acids, alternatively combination thereof. The difference of an amino acid sequence herein is allowed as long as an OXDC activity is not significantly reduced. A position being different in an amino acid sequence is not particularly limited as long as this condition is satisfied, or such differences may occur in plural sites. Plural herein means a number that corresponds to, for example, less than about 30% of the whole amino acid, preferably a number that corresponds to less than about 20%, more preferably a number that corresponds to less than about 10%, further more preferably a number that corresponds to less than about 5%, and the most preferably a number that corresponds to less than about 1%. That is, a homologous protein has a homology of, for example, about 70% or more to the amino acid sequence of the SEQ ID No. 15, preferably about 80% or more, more preferably about 90% or more, further more preferably 95% or more, and the most preferably about 99% or more.

A homologous protein is obtained preferably by generating conservative amino acid substitution in an amino acid residue that is not essential to OXDC activity. The "conservative amino acid substitution" herein refers to substitution of an amino acid residue having a side chain with the same properties for a certain amino acid residue. Amino acid residues are classified into some families, depending on side chains thereof, such as basic side chains (e.g., lysine, arginine, and histidine), acidic side chains (e.g., asparatic acid and glutamic acid), uncharged polar side chains (e.g., glycine, asparagine, glutamine, serine, threonine, tyrosine, and cysteine), non-polar side chains (e.g., alanine, valine, leucine, isoleucine, proline, phenylalanine, methionine, and tryptophan), β branched side chains (e.g., threonine, valine, and isoleucine), and aromatic side chains (e.g., tyrosine, phenylalanine, tryptophan, and histidine). Conservative amino acid substitution is preferably substitution between amino acid residues in the same family.

As a result of studies of the present inventors, it was revealed that a recombinant bacterium exerting high productivity can be obtained also when an oxdc gene connected with a yvrL gene is used. Thus, in one embodiment of the present invention, an expression vector containing a yvrL gene downstream of an oxdc gene originating in a microorganism is constructed. Then, a host is transformed with the expression vector to prepare a recombinant bacterium. Further, an OXDC production system using the recombinant bacterium is constructed. A specific example of a sequence of a yvrL gene is shown as the SEQ ID No. 5. A specific example of a sequence of a DNA fragment containing a yvrL gene downstream of an oxdc gene originating in a microorganism is shown as the SEQ ID No. 16. In one embodiment of the expression vector of the present invention, the DNA fragment is inserted.

By the way, various plasmid vectors for various host-vector systems are currently in the condition of being available. Examples of a plasmid vector having *Escherichia coli* as a host include pUC type plasmids and derivatives thereof, pBR322 type plasmids and derivatives thereof, pACYC type plasmids and derivatives thereof, and pSC101 type plasmids and derivatives thereof. Examples of a plasmid vector having a bacterium belonging to the genus *Bacillus* as a host include pUB110 (Gryczan, T. J. et al. J. Bacteriol. 134, 318-329 (1978)), pTA1060 (Bron, S. et al. Plasmid. 18, 8-15 (1987)), pC194 (Horinouchi, S. et al. J. Bacteriol. 150(2), 815-825 (1982)), and pE194 (Horinouchi, S. et al. J. Bacteriol. 150(2), 804-814 (1982)). A vector (shuttle vector) that can be reproduced with any of *Escherichia coli* and a bacterium belonging to the genus *Bacillus* is also available (Grande, G. et al. Monogr. (Dtsch. Ges. chem. Apparatewes). 105, 147-162 (1987); Truffaut, H. & Sebald, M. Biotechnol. Lett. 10, 1-6 (1988), Moriyama, H. et al. Nucleic Acids Res. 16, 8732 (1988); Bron, S. et al. Plasmid. 19, 231-241 (1988); Karp, M. Biochim. Biophys. Acta. 1007, 84-90 (1989), etc.)

The expression vector of the present invention can be constructed using plasmid vectors as described above. That is, a suitable plasmid vector (for example, a commercially available product) is selected in consideration of a relation with a host, thereafter inserting an α-amylase promoter belonging to the genus *Bacillus* and an oxdc gene originating in a microorganism in an embodiment of a desired arrangement, and the expression vector of the present invention can be thus obtained. When a plasmid vector having an α-amylase promoter belonging to the genus *Bacillus* can be obtained, an oxdc gene originating in a microorganism may be inserted so as to be arranged under the control of the α-amylase promoter. In the same manner, when a plasmid vector having an oxdc gene originating in a microorganism is obtained, an α-amylase promoter may be inserted in a position capable of controlling the gene.

When an α-amylase promoter belonging to the genus *Bacillus* and an oxdc gene originating in a microorganism (or either of them) are inserted in a plasmid vector, further modification such as deletion of an unnecessary sequence of a basic vector, addition of functional sequences (such as a selection marker and an enhancer), and the like may be added.

For operation methods, reagents, conditions, and the like, which are necessary when the expression vector of the present invention is constructed, for example, Molecular Cloning (Third Edition, Cold Spring Harbor Laboratory Press, New York) or Current protocols in molecular biology (edited by Frederick M. Ausubel et al., 1987) may be referred.

Preparation Method of Oxalate Decarboxylase Producing Bacteria, and Oxalate Decarboxylase Producing Bacteria When a suitable host bacterium is transformed with the expression vector of the present invention, a recombinant bacterium producing OXDC can be obtained. Accordingly, the present invention provides, as the second aspect, (1) a preparation method of an OXDC producing bacterium, characterized in transforming a host bacterium with the expression vector of the present invention, and (2) a recombinant bacterium obtained in the preparation method. The recombinant bacterium of the present invention has an expression plasmid vector containing an oxdc gene originating in a microorganism subjected to transcription control from an α-amylase promoter belonging to the genus *Bacillus*. The number of copies of the expression plasmid vector is not particularly limited and, for example, it is 1 to 700.

The host bacterium herein is not particularly limited, and is preferably *Escherichia coli* or a bacterium belonging to the genus *Bacillus*. Specific examples of *Escherichia coli* include JM109 strain, MC1061 strain, DH5α strain, and BL21 strain. On the other hand, examples of bacteria belonging to the genus *Bacillus* include *Bacillus subtilis, Bacillus licheniformis, Bacillus megaterium, Bacillus stearothermophilus, Bacillus brevis, Bacillus sphaericus, Bacillus polymyxa,* and *Bacillus alcalophilus*. Among these, *Bacillus subtilis* is preferable, and *Bacillus subtilis* 168 strain is particularly preferable.

Transformation may be performed using a conventional method in consideration of a host-vector system. When *Escherichia coli* is used as a host, it may be transformed in a competent cell method (for example, calcium chloride method, rubidium chloride method, Hanahan method, and SEM method), or an electroporation method. On the other hand, for transformation in the case where a bacterium belonging to the genus *Bacillus* is used as a host, a protoplast transformation method (see Chang, S. & Cohen, S. N. Mol. Gen. Genet. 168, 111-115 (1979), etc.), a competent cell method (see Spizizen, J. Proc. Natl. Acad. Sci. USA. 44, 1072-1078 (1958), etc.), or the like, can be used. According to the electroporation method, a plasmid vector can also be introduced into a bacterium that has not been plotoplasted, (Kusaoke, H. et al. Agric. Biol. Chem. 53, 2441-2446 (1989)).

In addition, a specific protocol of a transformation method is described in detail in, for example, Molecular Cloning, Third Edition, 1.84, Cold Spring Harbor Laboratory Press, New York.

Production Method of Oxalate Decarboxylase

A further aspect of the present invention relates to a production method of OXDC using the recombinant bacterium of the present invention. In the production method of the present invention, first, the recombinant bacterium of the present invention is cultured in the condition of inducing an α-amylase promoter (culture step). Subsequently, a step of recovering the produced OXDC is performed (recovery step).

The culture step is performed under "the condition of inducing an α-amylase promoter". Accordingly, a transcription activity due to the α-amylase promoter is exerted and an oxdc gene is expressed. The α-amylase promoter may be induced after elapse of a certain time from the start of culture. Timing of induction of the α-amylase promoter is not particularly limited, and from the viewpoint of increasing a yield of OXDC, the α-amylase promoter is preferably induced in the logarithmic growth phase or stationary phase. In particular, the α-amylase promoter is preferably induced between the late term of the logarithmic growth phase and the medium term of the stationary phase. However, in the case of a recombinant bacterium obtained using a bacterium belonging to the genus *Bacillus* and *Escherichia coli* as hosts, an α-amylase promoter may be induced at the start of culture. A person skilled in the art can set appropriate culture conditions according to preliminary experiments.

A culture liquid is sampled with time, and the number of bacteria is calculated according to a measurement of a turbidity (or absorbance) and the like so that growth stages (logarithmic growth phase, stationary phase, etc.) can be determined. It is surely acceptable that a growth curve is formed by preculture and a growth stage is determined utilizing the growth curve.

Other culture conditions (medium, culture temperature, culture time, etc.) may be suitably set in accordance with a recombinant bacterium provided in culture. For example, when a recombinant bacterium is *Escherichia coli*, modification may be added according to necessity on the basis of standard culture conditions. In addition, appropriate culture conditions can be set according to a preliminary experiment.

OXDC contains manganese (Mn) in its molecule. Therefore, when OXDC is produced by culturing a recombinant bacterium, it is required to use a medium added with manganese. As shown in Examples described later, as a result of studies made by the present inventors, when a recombinant bacterium obtained through transformation of *Escherichia coli* was used, high productivity was observed in the case of having a manganese concentration in a medium of 1 mM to 5 mM. The largest productivity was shown when the adding concentration was 5 mM. Accordingly, when a recombinant bacterium obtained through transformation of *Escherichia coli* is used, a manganese concentration in a medium is preferably 1 mM to 5 mM, and more preferably 5 mM, for the purpose of improvement in productivity. On the other hand, when a recombinant bacterium obtained through transformation of a bacterium belonging to the genus *Bacillus* is used, high productivity was observed in the case of having a manganese concentration in a medium of 0.1 mM to 1 mM. The largest productivity was shown when the adding concentration was 1 mM. Accordingly, when a recombinant bacterium obtained through transformation of a bacterium belonging to the genus *Bacillus* is used, a manganese concentration in a medium is preferably 0.1 mM to 1 mM, and more preferably 1 mM, for the purpose of improvement in productivity.

Composition of a medium is not particularly limited as long as the condition such that a recombinant bacterium provided in culture can be grown is satisfied, in addition to the condition of containing manganese in the medium. Examples of a carbon source in a medium including maltose, sucrose, gentiobiose, soluble starch, glycerin, dextrin, molasses, organic acids, and the like can be used. Examples of a nitrogen source including ammonium sulfate, ammonium carbonate, ammonium phosphate, ammonium acetate, or peptone, yeast extract, corn steep liquor, casein hydrolysate, bran, meat extract, and the like can be used. Examples of inorganic salts including potassium salt, magnesium salt, sodium salt, phosphate salt, manganese salt, iron salt, zinc salt, and the like can be used. A medium added with vitamins, amino acid, and like in order to improve growth of a recombinant bacterium may be used.

A pH of a medium is adjusted to, for example, about 3 to 8, preferably about 6 to 8, and culture is performed at a culture temperature of generally about 10 to 50° C., and preferably about 27 to 37° C. for about 1 to 15 days, and preferably about 1 to 3 days. When *Escherichia coli* is used as a host, culture is performed under the aerobic condition or the anaerobic condition. When a bacterium belonging to the genus *Bacillus* is used as a host, culture is performed under the aerobic condition. As a culture method, examples such as shake culture, rotary culture, and aerated and agitated culture can be utilized.

OXDC is recovered from a culture liquid or bacterial bodies in the recovery step subsequently to the culture step. When OXDC is recovered from a culture liquid, the culture supernatant is treated with, for example, filtration, centrifugation, etc. to thus remove insoluble substances, thereafter performing separation and purification suitably in combination with concentration with an ultra-filtration membrane, salting out such as ammonium sulfate precipitation, dialysis, and various types of chromatography, and OXDC can be thus obtained.

On the other hand, when OXDC is recovered from bacterial bodies, the bacterial bodies are crushed with, for example, a pressure treatment, an ultrasonic treatment, etc., thereafter performing separation and purification in the same manner as described above, and OXDC can be thus obtained. In addition, the above-described series of the steps (crush of bacterial bodies, separation, purification) may be performed after recovering the bacterial bodies from the culture liquid in advance through filtration, centrifugation, or the like.

EXAMPLES

1. Selection of oxdc Gene Expression System

Combination of hosts and promoters was examined for the purpose of improvement in productivity. For the hosts, (1) *Bacillus subtilis* 168 strain (ATCC (American Type Culture Collection)) that has been known as an OXDC producing bacterium and (2) *Escherichia coli* (*E. coli* JM109 strain (TAKARA BIO INC.)) that has generally been used for genetic recombination were selected. Promoters that can be expected to have high expression of introduced genes respectively were selected depending on these hosts (FIG. 1). In addition, an amy promoter is a promoter of an α-amylase gene. An α-amylase gene is a gene that many species of *Bacillus subtilis* (the genus *Bacillus*) have, and some genes cloned using an α-amylase promoter have been reported so far. On the other hand, a lac promoter is a general promoter used when *Escherichia coli* is used as a host, and has been known in a large expression amount.

2. Acquisition of oxdc Gene

An oxdc gene (yvrK) to be closed was obtained from a *Bacillus subtilis* 168 strain chromosome. Specifically, a chromosome DNA was firstly obtained from the *Bacillus subtilis* 168 strain using a conventional method. A primer set was designed on the basis of oxdc gene sequence information (SEQ ID No. 1) on the database (GenBank Accession No. Z99120). In addition, a restriction enzyme (XbaI) site was added to the 3' side primer.

```
3' side primer (primer 1):
                                    (SEQ ID No. 6)
5'-GGCTCTAGATTATTTACTGCATTTCTTTTTCAC-3'

5' side primer (primer 2, for amy promoter):
                                    (SEQ ID No. 7)
5'-AGGGAGAGGAAACATGAAAAAACAAAATGACATTCC-3'

5' side primer (primer 3, for lac promoter):
                                    (SEQ ID No. 8)
5'-GTCATTTTGTTTTTTCATAGCTGTTTCCTGTGTGAA-3'
```

The chromosome DNA obtained from the *Bacillus subtilis* 168 strain was used as a template and PCR was performed using these primers to obtain a desired oxdc gene.

3. Acquisition of amy Promoter

An amy promoter originating in *Bacillus amyloliquefaciens* was used. Firstly, a chromosome DNA was obtained from *Bacillus amyloliquefaciens* using a conventional method. A primer that specifically amplifies a promoter region (the SEQ ID No. 2) was designed in reference to a sequence of an α-amylase gene (GenBank Accession No. J01542) on database. In addition, a restriction enzyme site of EcoRI was added to the 5' side primer. A primer containing an amy promoter 3' terminal sequence and an oxdc gene 5' terminal sequence was used as the 3' side primer.

```
5' side primer (primer 4):
                                    (SEQ ID No. 9)
5'-CGCCGAATTCTGGATCGATTGTTTGAG-3'

3' side primer (primer 5):
                                    (SEQ ID No. 10)
5'-GTCATTTTGTTTTTTCATGTTTCCTCTCCCTCTCATTTTC-3'
```

A chromosome DNA of prepared *Bacillus amyloliquefaciens* was used as a template and PCR was performed using the designed primers to obtain a DNA fragment of the amy promoter.

4. Preparation of Shuttle Vector pUBC1 (FIG. 2)

A pUB110 vector (ATCC (American Type Culture Collection)) that was generally used in a genus *Bacillus* expression system was employed when the *Bacillus subtilis* 168 strain was used as a host. The pUB110 vector was not used as it is, but first considering that an expression plasmid was constructed in *Escherichia coli* in order to improve transformation efficiency in construction of a recombinant bacterium, a shuttle vector with plasmid vectors for *Escherichia coli*, pUC18 and pUB110, was constructed. Actually, pUC18 and pUB110 were treated with restriction enzymes, AflIII and XbaI, and fragments containing reproduction initiation regions of each vector were obtained. Subsequently, the obtained fragments were ligated each other with ligase to form a shuttle vector pUBC1.

Figure 3:
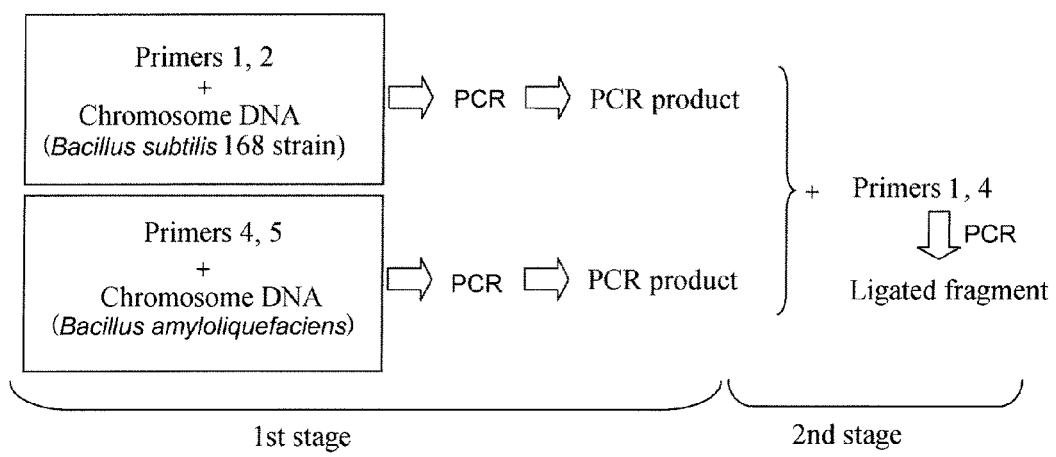
FIG. 3 illustrates an operation procedure for connecting an amy promoter and an oxdc gene.

5. Connection of amy Promoter and oxdc Gene (FIG. 3)

An amy promoter to be inserted and an oxdc gene were ligated in PCR. PCR (1st stage) was first performed in the method described in the column 2. (primers 1 and 2 were used) and the method described in the column 3. (primers 4 and 5 were used), respectively. The PCR products were mixed and PCR (2nd stage) was then performed using the primers 1 and 4 to obtain a fragment in which an oxdc gene was connected right after the amy promoter (amy promoter-oxdc gene ligated fragment).

Figure 4:
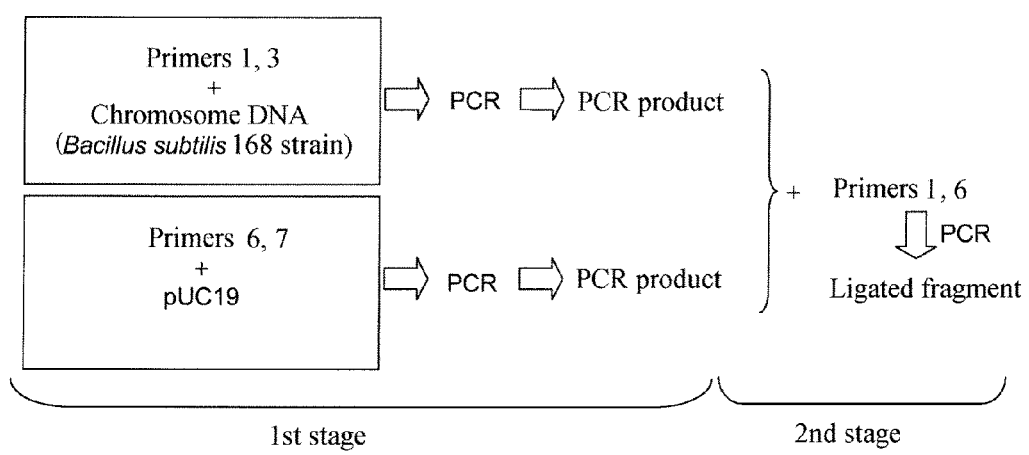
FIG. 4 illustrates an operation procedure for connecting a lac promoter and an oxdc gene.

6. Connection of lac Promoter and oxdc Gene (FIG. 4)

When *Escherichia coli* was used as a host and an oxdc gene was introduced downstream of a lac promoter, pUC19 that is a high copy vector was employed. Firstly, a 5' side primer containing an AflIII restriction enzyme site, which is present upstream of the lac promoter, was designed.

```
5' side primer (primer 6):
                                    (SEQ ID No. 11)
5'-CTTTTGCTCACATGTTCTTTCCTG-3'
```

On the other hand, a 3' side primer containing a lac promoter 3' terminal sequence and an oxdc gene 5' terminal sequence was designed.

```
3' side primer (primer 7):
                                    (SEQ ID No. 12)
5'-TTCACACAGGAAACAGCTATGAAAAAACAAAATGAC-3'
```

PCR (1st stage) was first performed in the method described in the column 2. (primers 1 and 3 were used). A lac promoter (pUC19) was used as a template and PCR (1st stage) was performed using primers 6 and 7. PCR products obtained from the PCR in the first stage were mixed and PCR (2nd stage) was then performed using the primers 1 and 6 to obtain a DNA fragment in which an oxdc gene was connected right after the lac promoter.

7. Construction of Recombinant Bacterium (OXDC Producing Bacterium)

(1) Recombinant Bacterium No. 1

Figure 5:
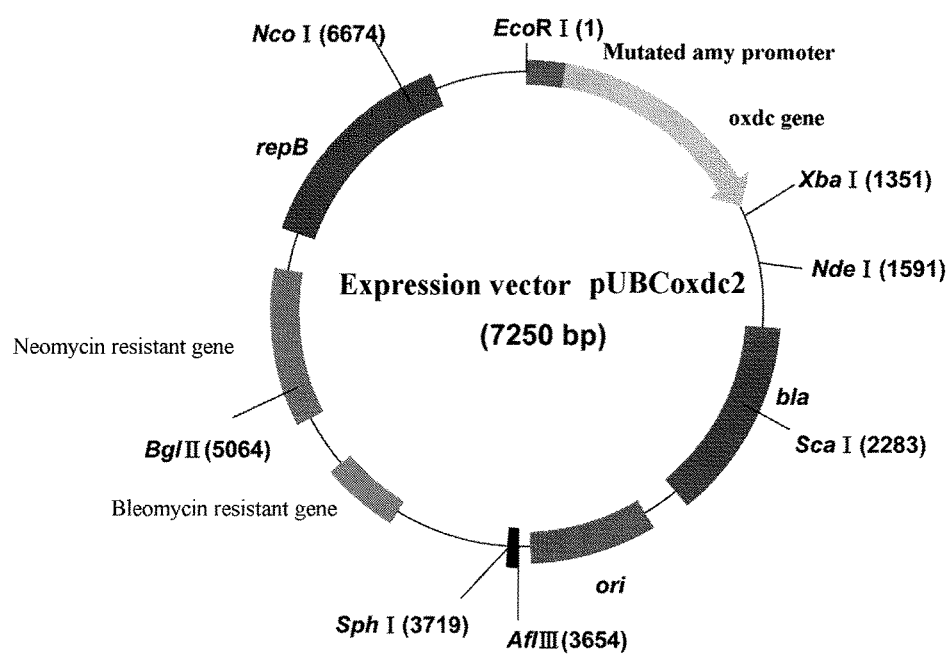
FIG. 5 shows a structure of oxdc gene expression plasmid vector pUBCoxdc2.

The shuttle vector pUBC1 and amy promoter oxdc gene ligated fragment was treated with EcoRI and XbaI, and then ligated with ligase to thus obtain an oxdc gene expression plasmid vector, pUBCoxdc2 (FIG. 5). Subsequently, *Escherichia coli* JM 109 strain was transformed with the vector. The vector was prepared in a large amount with the recombinant *Escherichia coli*, and the *Bacillus subtilis* 168 strain was then transformed with the vector in the protoplast-PEG-fusion method to form an oxdc gene recombinant bacterium.

Figure 6:
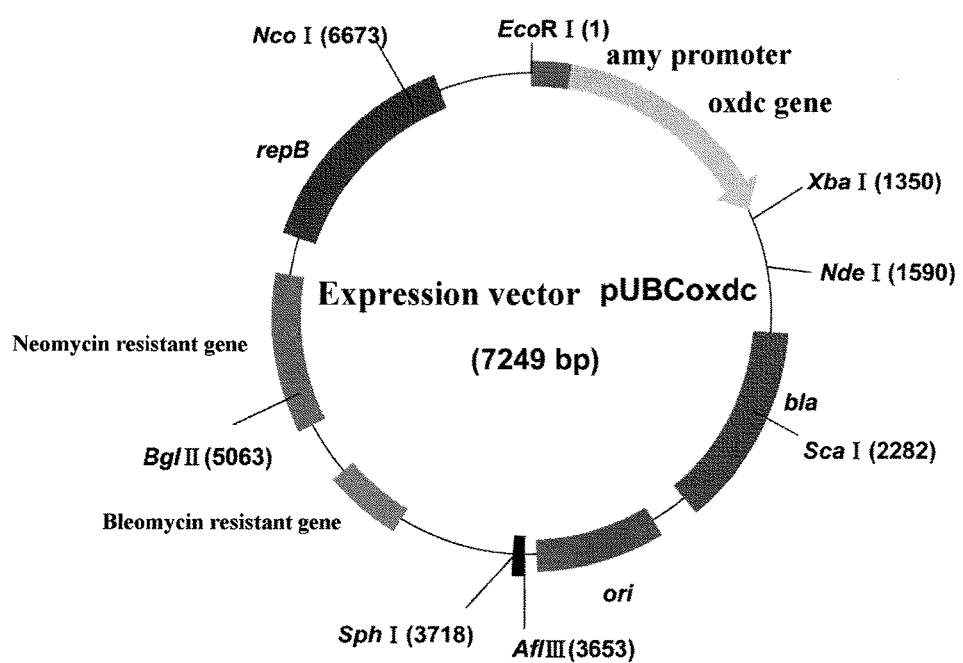
FIG. 6 shows a structure of oxdc gene expression plasmid vector pUBCoxdc.

When the base sequence of the inserted fragment of the oxdc gene expression plasmid vector retained in the oxdc gene recombinant bacterium was examined, it was revealed that variation of 3 bases were contained in the amy promoter (mutated amy promoter: SEQ ID No. 4). In reference to the sequence of the wild type amy promoter registered in public database, a promoter (amy promoter: SEQ ID No. 3) that has the same sequence as the sequence of the wild type amy promoter was formed by substitution and insertion of a region where the variation is included (substitution and deletion were performed using a Quick Change Site-Directed Mutagenesis Kit manufactured by Stratagene Co.). The Bacillus subtilis 168 strain was again transformed with the oxdc gene expression plasmid vector pUBCoxdc (FIG. 6) after such operations to thus obtain a desired oxdc gene recombinant bacterium No. 1.

Figure 7:
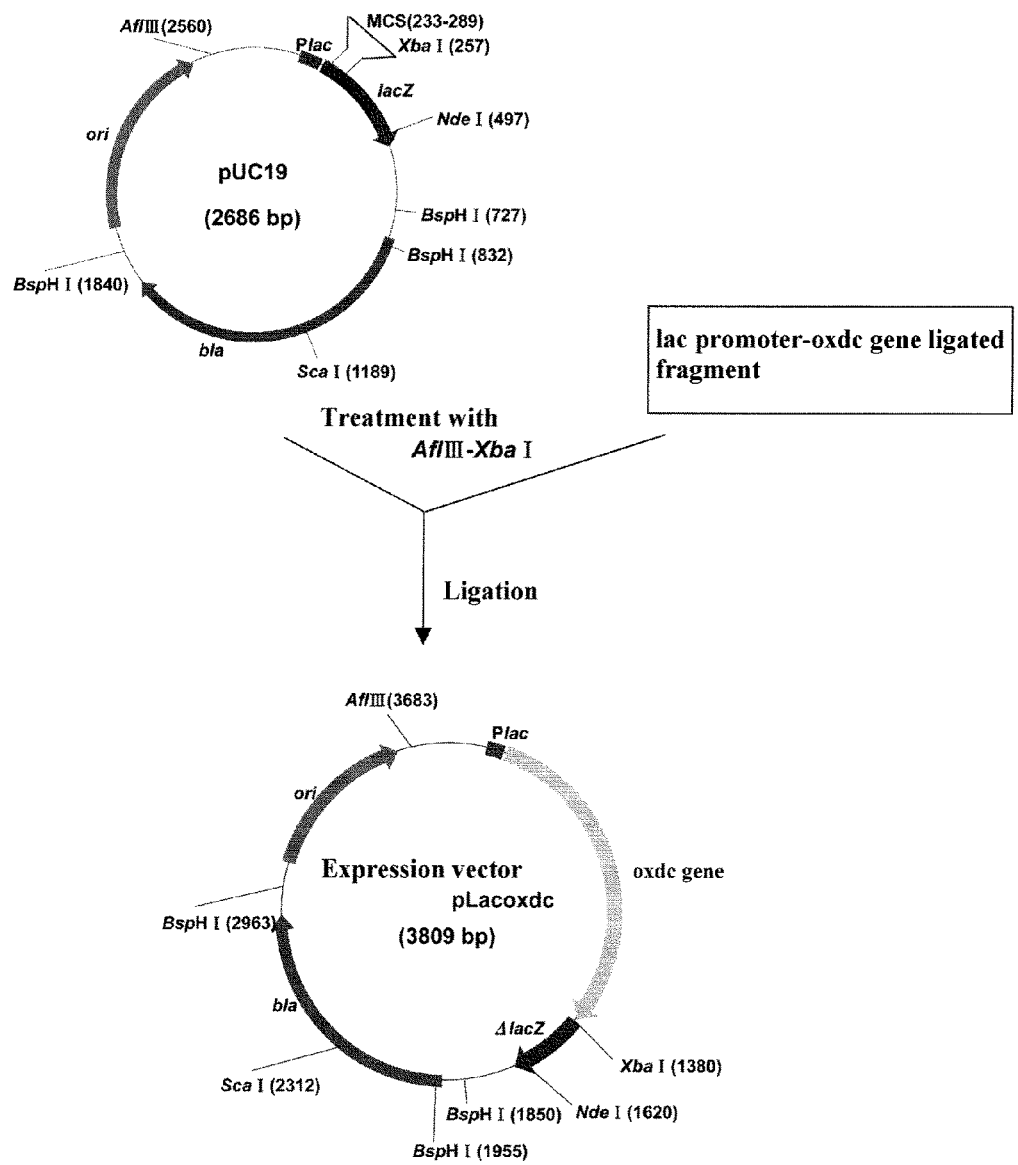
FIG. 7 shows a construction method and a structure of oxdc gene expression plasmid vector pLacoxdc.

(2) Recombinant Bacterium No. 2 pUC19 and a lac promoter oxdc gene ligated fragment were treated with AflIII-XbaI and then ligated with ligase to thus obtain an oxdc gene expression plasmid vector pLacoxdc (FIG. 7). The *Escherichia coli* JM109 strain was transformed with the vector using a conventional method. As in the described manner, the recombinant bacterium No. 2 having the oxdc gene expression plasmid vector pLacoxdc was obtained, using *Escherichia coli* as a host.

(3) Recombinant Bacterium No. 3

The expression plasmid vector pUBCoxdc2 (FIG. 5) that has the mutated amy promoter described in the column (1) was prepared in a large amount with *Escherichia coli* JM109 strain. Subsequently, *Bacillus subtilis* 168 strain was transformed with the vector in a protoplast-PEG-fusion method to thus obtain a recombinant bacterium No. 3.

(4) Recombinant Bacterium No. 4

A functionally unknown gene that is called a yvrL gene is present downstream of the oxdc gene on a chromosome DNA of a *Bacillus subtilis* 168 strain, and transformation was tried including the gene as well. Firstly, a 3' side primer to amplify a sequence containing an oxdc gene and a yvrL gene was designed. In addition, a restriction enzyme XbaI site was added to the outer side of the yvrL gene 3' terminal in the primer.

```
3' side primer (primer 8):
                              (SEQ ID No. 13)
5'-TTATCTAGAGCTTGCTTCCGTCTATCAAGG-3'
```

Figure 8:
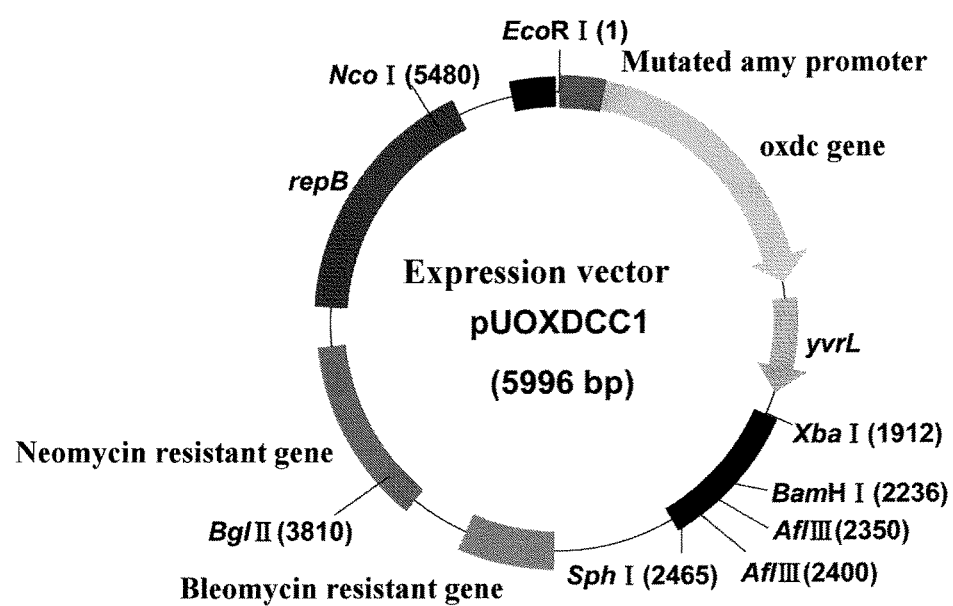
FIG. 8 shows a structure of oxdc gene expression plasmid vector pUOXDCC1.

A *Bacillus subtilis* 168 strain chromosome DNA was used as a template, and PCR (1st stage) using the primer 8, and the primer 2 as a 5' side primer was performed. On the other hand, PCR (1st stage) was performed in the procedure described in the column 2. The PCR products obtained in PCR in the 1st stage were mixed and PCR (2nd stage) was then preformed using the primers 4 and 8, to thus obtain a DNA fragment in which an oxdc gene was arranged downstream of the amy promoter and a yvrL gene was arranged further downstream. The obtained fragment and pUB110 were treated with EcoRI and XbaI. The DNA fragment after treatment with the restriction enzymes was ligated to obtain an oxdc expression plasmid vector pUOXDCC1 (FIG. 8). The *Bacillus subtilis* 168 strain was transformed with the vector in a protoplast-PEG-fusion method to thus obtain a recombinant bacterium No. 4.

(5) Recombinant Bacterium No. 5

Firstly, a shuttle vector pCUHB-1 having a reproduction initiation region which functions in *Escherichia coli* and *Bacillus subtilis* was prepared. pC194 (ATCC (American Type Culture Collection)) was treated with ClaI, and pUC19 was treated with BbiII, respectively, and the both were then ligated (vector 1). In addition, pHV1249 (Bacillus Genetic Stock Center) was treated with NcoI and then ligated with a NcoI site, to thus obtain a vector defected with the inside of the NcoI site (vector 2). The vector 1 and the vector 2 were treated with ApaLI and the both were then ligated (vector 3). The vector 3 was partially decomposed with EcoRI and a DNA fragment at around 5.7 to 5.8 kbp was recovered. The recovered DNA fragment was ligated, then treated with AvaII and ligated again (vector 4). The vector 4 was treated with SmaI and blunted, and pBEST501 (Non-patent Document 3: Nucleic Acids Research, Volume 17, Number 11, p 4410, 1989) was treated with EcoRI-PstI and blunted, and the both were then ligated to thus obtain a vector pCUHB-1 (upper column in FIG. 9).

An amy promoter-oxdc gene ligated fragment to be inserted was prepared as described below. A primer added with a restriction enzyme site that is a HindIII site in the outside of the amy promoter 5' terminal was designed.

Figure 9:
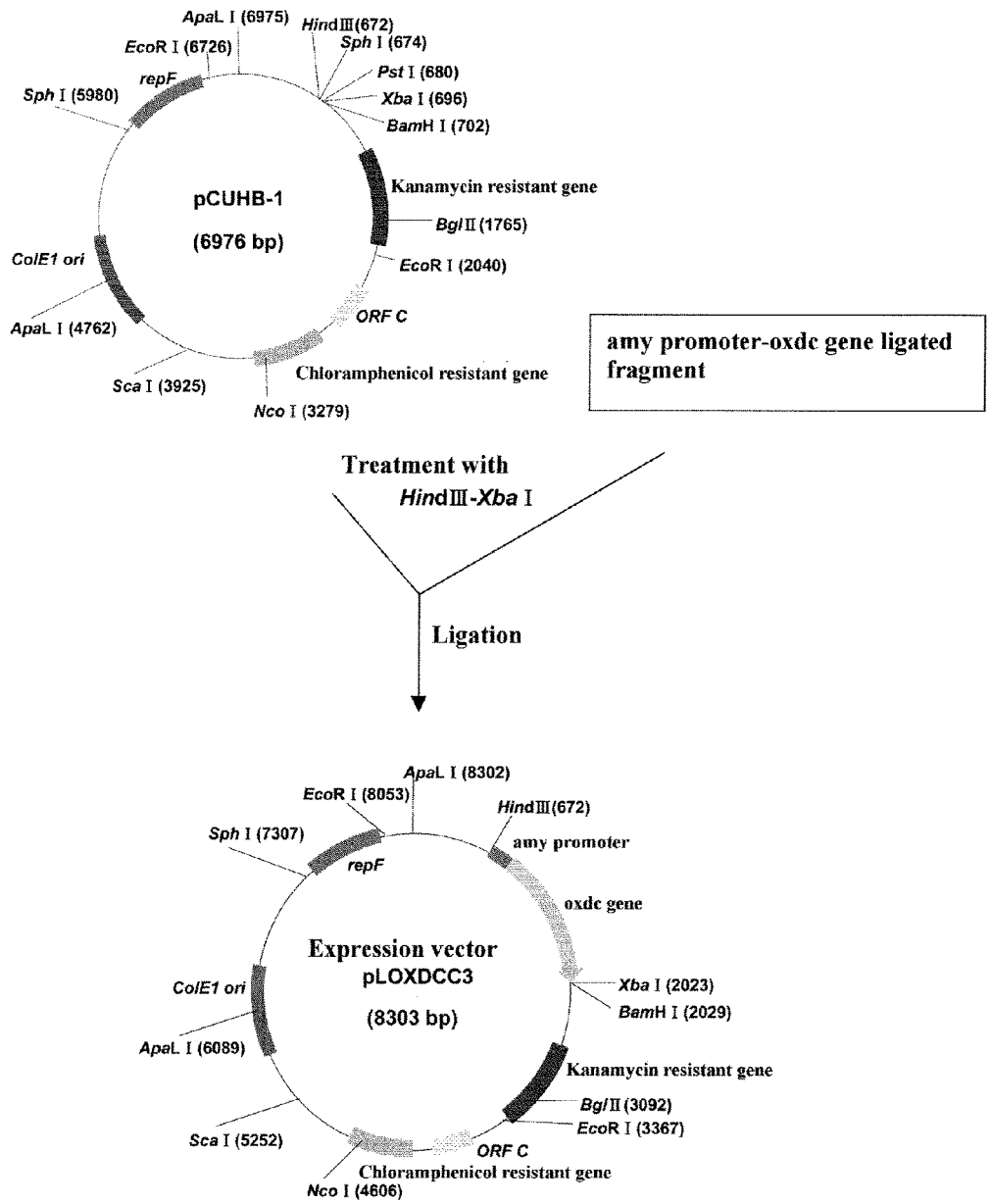
FIG. 9 shows a construction method and a structure of oxdc gene expression plasmid vector pLOXDCC3.

```
5' side primer (primer 9):
                              (SEQ ID No. 14)
5'-CTTAAGCTTTGGATCGATTGTTTGAGA-3'
``` pUBCoxdc was used as a template, and PCR was preformed using the primer 1 and the primer 9. Accordingly, an amy promoter-oxdc gene ligated fragment in which a HindIII site was added to the 5' terminal and a XbaI site was added to the 3' terminal (HindIII-amy promoter-oxdc gene-XbaI) was obtained. This fragment was treated with HindIII-XbaI, and on the other hand, pCHUB-1 was treated with HindIII-XbaI in the same manner, and they are ligated each other to obtain an oxdc expression plasmid vector pLOXDCC3 (FIG. 9). The *Escherichia coli* JM109 strain was transformed with the vector to thus obtain a recombinant bacterium No. 5.

(6) Recombinant Bacterium No. 6

A mutated amy promoter-oxdc gene ligated fragment to be inserted was prepared as described below.

Figure 10:
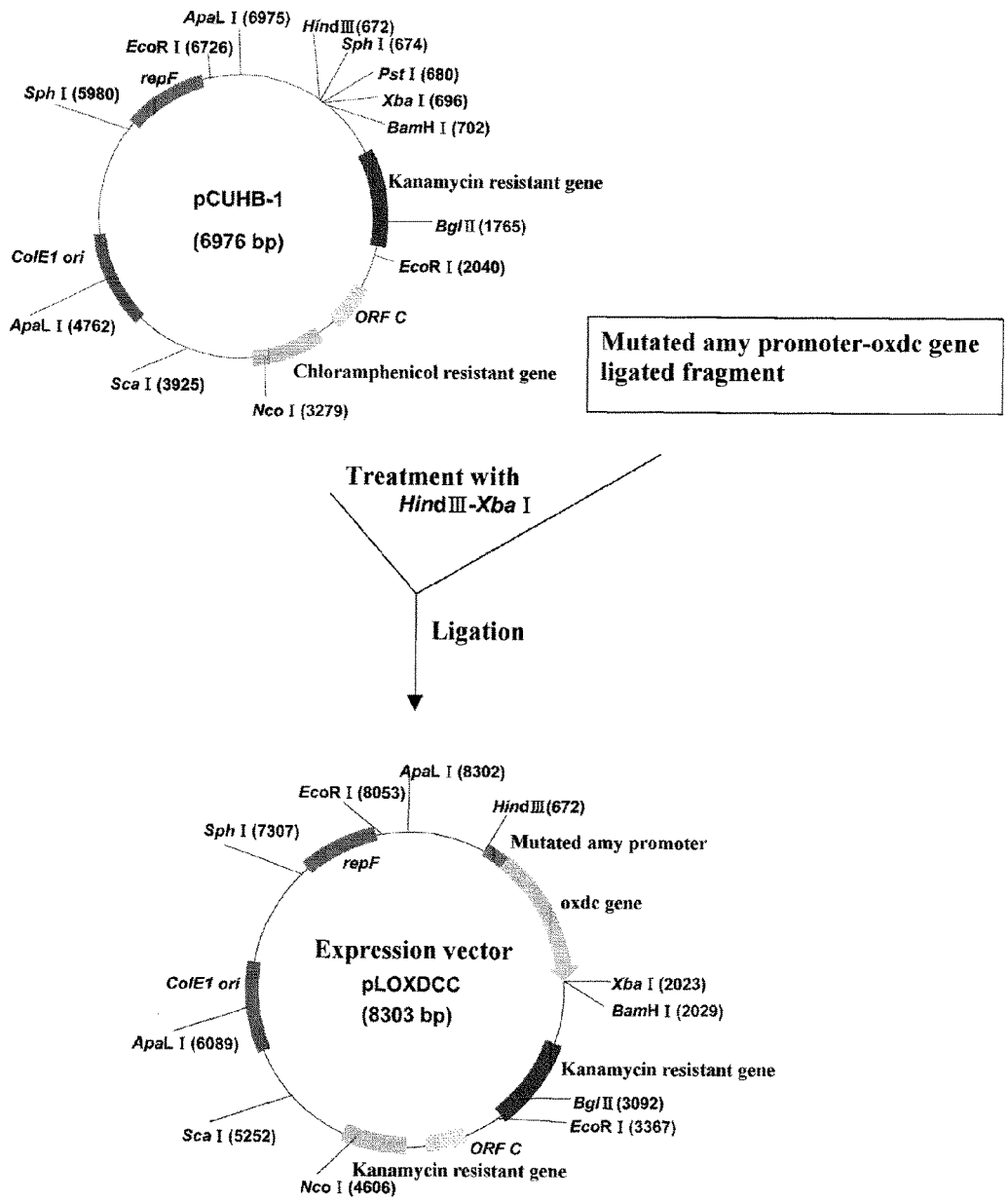
FIG. 10 shows a construction method and a structure of oxdc gene expression plasmid vector pLOXDCC.

A *Bacillus amyloliquefaciens* chromosome DNA was used as a template, and PCR (1st stage) was performed using the primer 9 and the primer 5. On the other hand, a *Bacillus subtilis* 168 strain chromosome DNA was used as a template and PCR (1st stage) was performed using the primer 1 and the primer 2. The PCR products obtained in PCR in the 1st stage were mixed and PCR (2nd stage) was then preformed using the primer 1 and the primer 9 to obtain a ligated fragment of a mutated amy promoter and an oxdc gene. This ligated fragment and a vector pCUHB-1 were treated with a restriction enzyme HindIII-XbaI and the both were then ligated to obtain an oxdc expression plasmid vector pLOXDCC (FIG. 10). The *Escherichia coli* JM109 strain was transformed with the vector to thus obtain a recombinant bacterium No. 6.

8. Culture Method of Recombinant Bacterium

In order to examine OXDC productivity of the recombinant bacteria Nos. 1 to 6, a liquid medium was prepared based on an LB medium. A specific culture method will be described below.

Firstly, 5 mL of the following medium for preculture was used to perform preculture (test-tube culture at 37° C. for one night). Antibiotics were added depending on chemical resistance of the recombinant bacteria. Specifically, kanamycin was added to the recombinant bacteria No. 1, 3, 4, 5, and 6

(final concentration 25 μg/mL), and ampicillin was added to the recombinant bacterium No. 2 (final concentration 50 μg/mL).

<Medium for Preculture (Common in All Recombinant Bacterium)>

Bacto Yeast Extract (made by Becton, Dickinson and Company) 0.5%

Bacto Tryptone (made by Becton, Dickinson and Company) 1%

NaCl 0.5%

Next, 50 mL of the following medium for main culture was prepared in a 300 mL-baffled Erlenmeyer flask, 1% amount of the preculture liquid was then added thereto, and shake culture was performed at 37° for one night (up to 24 hours) (main culture). Herein, since an amylase promoter is induced with saccharides of disaccharides or polysaccharides, the recombinant bacteria (No. 1, 3, 4, 5, and 6) which have amy promoters in expression plasmids were added with maltose (final concentration 1%) and $MnCl_2$ (0.1 mM in the case of hosts belonging to the genus *Bacillus*, 5 mM in the case of *Escherichia coli* hosts) in inoculation. On the other hand, the recombinant bacterium (No. 2) which has a lac promoter in an expression plasmid was added with IPTG (final concentration 1 mM) when the culture turbidity $A_{660}$ was 0.3 to 0.6 to induce the lac promoter. In this time, $MnCl_2$ (5 mM) was added together.

<Medium for Main Culture (LB Medium)>

Bacto Yeast Extract (made by Becton, Dickinson and Company) 0.5%

Bacto Tryptone (made by Becton, Dickinson and Company) 1%

NaCl 0.5%

By the way, since OXDC contains manganese in its molecule, when an oxdc gene recombinant bacterium was cultured to produce OXDC, manganese was required to be added to a medium. Thus, an optimal concentration of manganese to be added was also studied from the viewpoint of improvement in OXDC productivity, in a recombinant bacterium having an expression plasmid vector inserted with a ligated fragment of an amy promoter and an oxdc gene.

9. OXDC Productivity of Recombinant Bacteria

OXDC was produced in bacterial bodies of the oxdc gene recombinant bacteria Nos. 1 to 6. Depending on conditions, only soluble OXDC, only insoluble (inclusion body) OXDC, or both of soluble OXDC and insoluble (inclusion body) OXDC were produced. In order to examine productivity of OXDC, bacteria after culture were collected and crushed to thus recover OXDC in the bacterial bodies. Actually, the bacterial bodies after culture were recovered from culture liquids through centrifugation, and then washed with a suitable amount of a buffer solution to remove medium components. Then, glass beads and a suitable amount of a buffer solution were added to the obtained recombinant bacteria to perform bacterial body crush with Multi Beads Shocker (Yasui Kikai Corporation) (for 600 seconds in a cycle of operation for 60 seconds and rest for 30 seconds, rotational number of 2000 rpm). OXDC is contained in a supernatant after crushing bacterial bodies when produced as being soluble, whereas OXDC is contained in a precipitate after crushing bacterial bodies when produced as being insoluble. Accordingly, OXDC in the supernatant or precipitate of bacterial bodies crush was measured in the following method and productivity of each recombinant bacterium was found.

Figure 11:
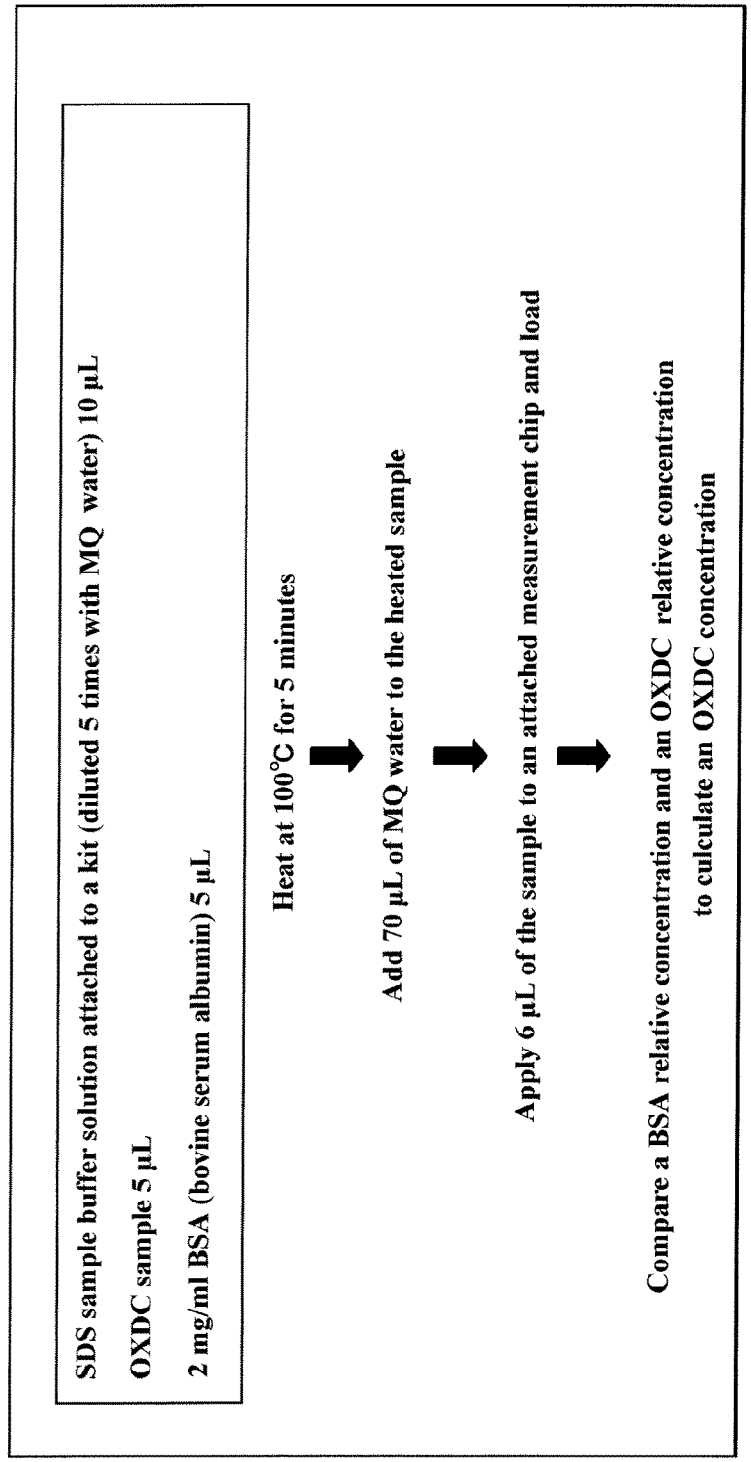
FIG. 11 illustrates an operation procedure of a measurement method of an OXDC concentration.

An OXDC concentration in a supernatant after crushing bacterial bodies or a precipitate after crushing bacterial bodies was confirmed by using Agilent 2100 Bioanalyzer (manufactured by Agilent Technologies) (FIG. 11). A sample (regardless of soluble or insoluble one) was thermally treated, adding an attached treatment liquid, and then supplied to an attached chip filled with a gel to thus detect a protein as a peak. Since the size of the peak was proportional to a protein concentration, BSA (bovine serum albumin) having an appropriate concentration was added to the sample as the internal standard substance, and the protein concentration in the sample can be thus calculated. A concentration of OXDC after crushing bacterial bodies was measured using the above-described method.

Figure 12:
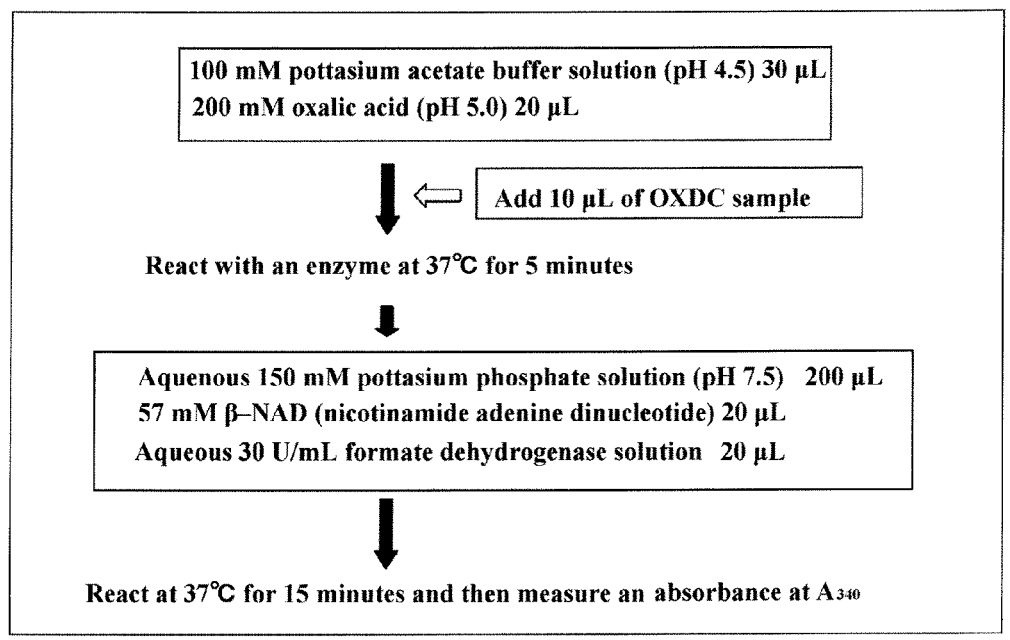
FIG. 12 illustrates an operation procedure of a measurement method of a qualitative OXDC activity.

An activity of OXDC was also measured for confirmation of qualitative productivity. A measurement of the OXDC activity was performed in a measurement method based on the following principle (FIG. 12). When OXDC acted in the presence of oxalic acid, oxalic acid was decomposed to produce formic acid. The produced formic acid was decomposed with formate dehydrogenase having NAD as a coenzyme and a generated amount of NADH generated in the reaction was measured at an absorption wavelength $\lambda_{340}$ specific to NADH and converted to an active value.

By the way, OXDC was produced as a soluble or insoluble inclusion body. Therefore, when OXDC was produced as an insoluble inclusion body, it cannot be directly measured and a step of solubilization and refolding is required as a treatment prior to a measurement as shown below. When OXDC was produced as a soluble inclusion body, a supernatant of bacterial bodies crush may be directly supplied to an activity measurement system.

Firstly, solubilization of an inclusion body OXDC was performed in 1 M guanidine hydrochloride. Specifically, a suitable amount of a solution of 1 M guanidine hydrochloride was added to a precipitate recovered after crushing bacterial bodies (including inclusion body OXDC) and suspended well. Thereby, the inclusion body OXDC was solubilized in the solution. Then, the solution of 1 M guanidine hydrochloride containing the solubilized OXDC was diluted 5 times with a buffer solution. This dilution step allows OXDC to be refolded so that OXDC takes a structure as an active body. An activity measurement was performed using the OXDC sample treated with such solubilization and refolding. In addition, efficiency of solubilization and refolding was not constant in every time, and also, ratios of solubility and insolubility were not necessarily constant; therefore, it was considered that a precise evaluation of the OXDC activity in the sample was difficult. Thus, a quantitative method using the above-described Agilent 2100 Bioanalyzer was used in combination to examine productivity of each recombinant bacterium.

10. Comparison of OXDC Productivity

Results of measuring productivity of each recombinant bacterium were shown in FIG. 13. All of the oxdc gene recombinant bacteria (recombinant bacteria Nos. 1, 3 and 4) having expression plasmid vectors ligated with oxdc genes downstream of amy promoters (or mutated amy promoters), using *Bacillus subtilis* 168 strains as hosts, showed very high OXDC productivity (3,250 to 5,425 times of *Bacillus subtilis* 168 wild type strain No. 7, 19.3 to 36.9 times of reported recombinant *Escherichia coli* No. 8).

Herein, in the case of a recombinant bacterium that produces a desired substance in the bacterial body, it is generally difficult to attain very high productivity. For example, when *Escherichia coli* is used as a host, it has been considered to be very difficult to attain productivity that exceeds 1 g/L. In consideration of the fact, productivity of the recombinant bacteria of this time can be evaluated to be very high as recombinant bacteria producing a desired substance in the bacterial bodies. In particular, productivities of recombinant bacteria No. 1, 3 and 4 are astonishing (1 g/L or more in Nos. 1 and 4, even 2 g/L or more in No. 3) and thus worthy of special mention. The fact that the recombinant bacteria No. 1, 3 and 4 showed very high productivity also means that to express combination of an amy promoter and an oxdc gene in a bacterial body is highly effective to OXDC productivity.

On the other hand, oxdc gene recombinant bacteria (recombinant bacteria Nos. 5 and 6) having expression plasmid vectors ligated with oxdc genes downstream of amy promoters (or mutated amy promoters), using *Escherichia coli* as hosts, also showed very high OXDC productivity (495 to 900 times of *Bacillus subtilis* 168 wild strain No. 7, 3.7 to 6.3 times of reported *Escherichia coli* No. 8). Their productivity was beyond the productivity of the recombinant bacterium No. 2 using a lac promoter.

The above-described results showed that an amy promoter originating in *Bacillus* is effective as a promoter for highly producing OXDC, regardless of any host.

On the other hand, as comparing productivity between the recombinant bacterium No. 1 and the recombinant bacterium No. 3, or between the recombinant bacterium No. 5 and the recombinant bacterium No. 6, it was found that a case of using a mutated amy promoter has higher oxdc productivity than a case of using a wild type amy promoter. From this result, it can be concluded that using a mutated promoter is effective to improvement in productivity.

Also, comparison of productivity between the recombinant bacterium No. 3 and the recombinant bacterium No. 4 revealed that, even though productivity is reduced due to presence of a yvrL gene downstream of an oxdc gene, still high productivity can be attained.

Figure 14:
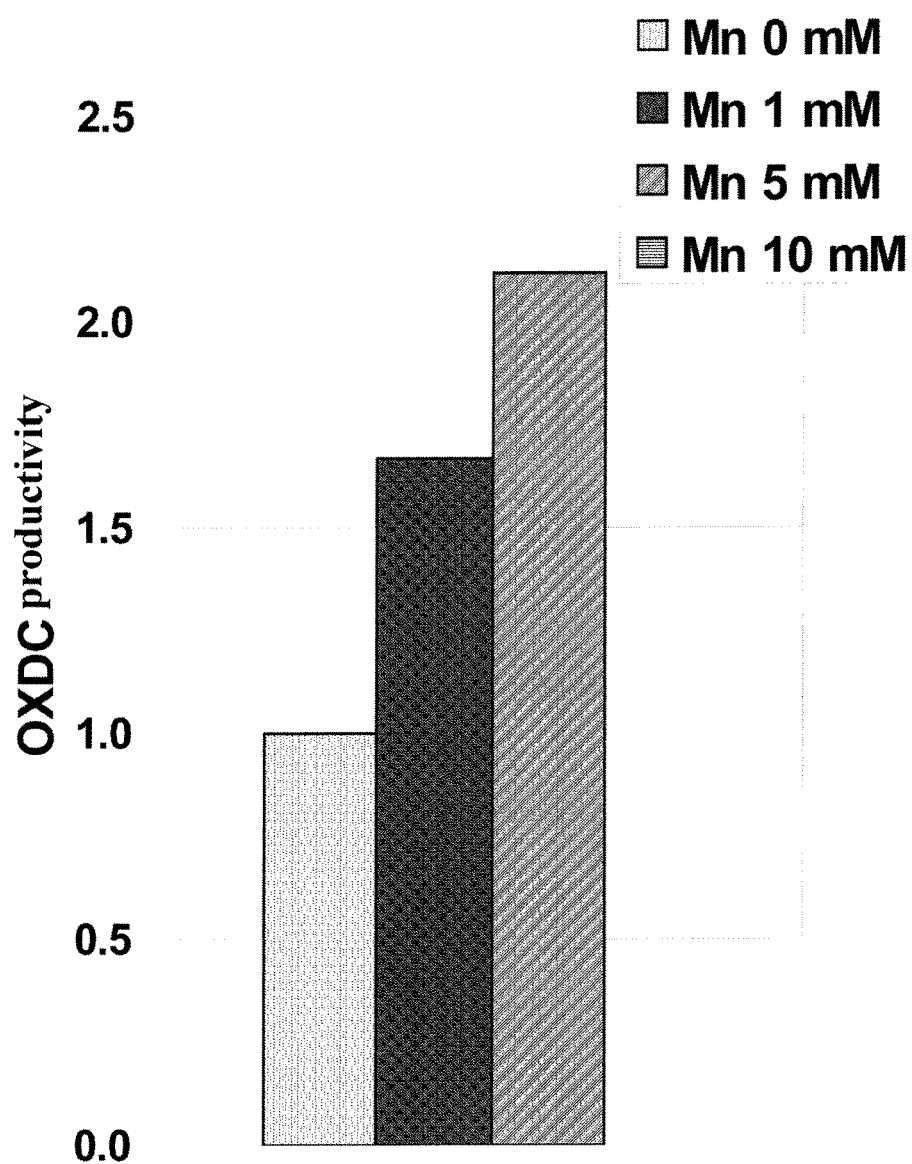
FIG. 14 is a graph showing a relation between a manganese concentration in a medium and OXDC productivity when the recombinant bacterium No. 5 was used as a relative value when OXDC productivity in the case of having an added manganese concentration of 0 mM was assumed to be 1.
Figure 15:
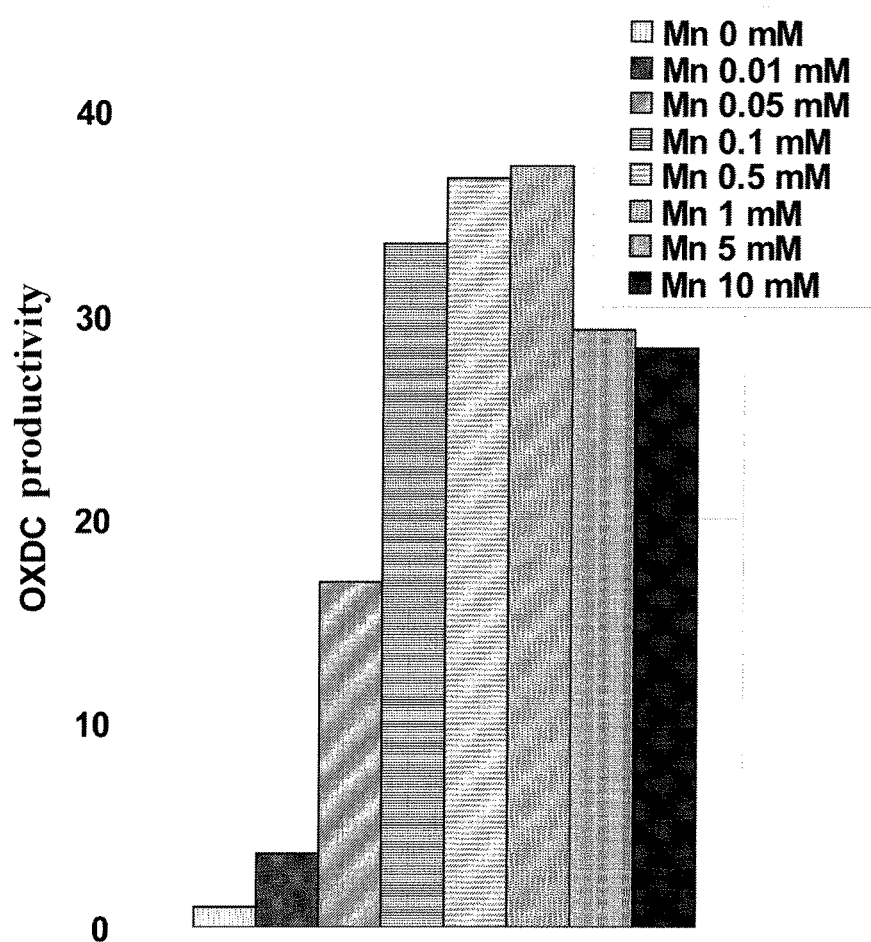
FIG. 15 is a graph showing a relation between a manganese concentration in a medium and OXDC productivity when the recombinant bacterium No. 1 was used as a relative value when OXDC productivity in the case of having an added manganese concentration of 0 mM was assumed to be 1.

Further, as a result of studying relationship between a manganese concentration and productivity in a medium, when a manganese concentration in a medium was 1 to 5 mM in the case where *Escherichia coli* was a host (recombinant bacterium No. 5), very high OXDC productivity was observed, and when the manganese concentration was 5 mM, OXDC productivity reached maximum (FIG. 14). On the other hand, very high OXDC productivity was observed at a manganese concentration of 0.1 to 1.0 mM in the case where a host was a *Bacillus subtilis* 168 strain (recombinant bacterium No. 1), and OXDC productivity reached maximum at a manganese concentration of 1.0 mM (FIG. 15).

INDUSTRIAL APPLICABILITY

The present invention is utilized to highly produce OXDC originating in microorganisms.

The invention is not limited to description of the embodiments and examples of the present invention described above at all. Various modified embodiments are also included in the invention within the range which does not depart from description of the scope of the patent claims and can be easily conceived of by a person skilled in the art.

Contents of treatises, unexamined patent publication bulletins, and examined patent publication bulletins clearly expressed in the specification are all incorporated herewith by their references.

The invention claimed is:

1. A method for producing a recombinant oxalate decarboxylase, comprising:
   a step of culturing a recombinant bacterium obtained by transforming a bacterium belonging to the genus *Bacillus* or to the species *Escherichia coli* with a recombinant expression plasmid vector comprising an α-amylase promoter having the DNA sequence set forth in any one of SEQ ID Nos. 2 to 4 and an oxalate decarboxylase gene originating in a microorganism that is provided under the control of the α-amylase promoter in a medium having a manganese concentration of 0.1 mM to 1 mM when the bacterium belongs to the genus *Bacillus* or a manganese concentration of 1 mM to 5 mM when the bacterium belongs to the species *Escherichia coli*; and
   a step of recovering the oxalate decarboxylase thus produced.

2. The method according to claim 1, wherein the microorganism is a bacterium belonging to the genus *Bacillus*.

3. The method according to claim 1, wherein the microorganism is *Bacillus subtilis*.

4. The method according to claim 1, wherein the microorganism is a *Bacillus subtilis* 168 strain.

5. The method according to claim 1, wherein the oxalate decarboxylase gene originating in a microorganism comprises the DNA sequence set forth in SEQ ID No. 1.

6. The method according to claim 1 comprising a yvrL gene downstream of the oxalate decarboxylase gene originating in a microorganism.

7. The method according to claim 6, wherein the recombinant expression plasmid vector includes a yvrL gene comprising the DNA sequence set forth in SEQ ID No. 5.

8. The method according to according to claim 6 comprising a DNA fragment of the sequence set forth in SEQ ID No. 16.

9. The method according to claim 1, wherein the bacterium belonging to the genus *Bacillus* is *Bacillus subtilis*.

10. The method according to claim 1, wherein the bacterium belonging to the genus *Bacillus* is *Bacillus subtilis* 168 strain.

11. The method according to claim 1, wherein the bacterium belongs to the species *Escherichia coli*.

12. The method according to claim 1, wherein the α-amylase promoter has the DNA sequence set forth in SEQ ID No. 2.

13. The method according to claim 1, wherein the α-amylase promoter has the DNA sequence set forth in SEQ ID No. 3.

14. The method according to claim 1, wherein the α-amylase promoter has the DNA sequence set forth in SEQ ID No. 4.

15. The method according to claim 12, wherein the oxalate decarboxylase gene originating in a microorganism has the DNA sequence set forth in SEQ ID No. 1.

16. The method according to claim 12, wherein the recombinant expression plasmid vector comprises a DNA fragment having the sequence set forth in SEQ ID No. 16.

17. The method according to claim 13, wherein the oxalate decarboxylase gene originating in a microorganism has the DNA sequence set forth in SEQ ID No. 1.

18. The method according to claim 13, wherein the recombinant expression plasmid vector comprises a DNA fragment having the sequence set forth in SEQ ID No. 16.

19. The method according to claim 14, wherein the oxalate decarboxylase gene originating in a microorganism has the DNA sequence set forth in SEQ ID No. 1.

20. The method according to claim 14, wherein the recombinant expression plasmid vector comprises a DNA fragment having the sequence set forth in SEQ ID No. 16.

* * * * *